United States Patent
Gondal et al.

(10) Patent No.: US 11,635,386 B2
(45) Date of Patent: Apr. 25, 2023

(54) **QUANTIFICATION OF THE MICRONUTRIENT PROFILE IN *MORINGA OLEIFERA* TREE LEAVES USING CALIBRATION FREE LASER INDUCED BREAKDOWN SPECTROSCOPY**

(71) Applicants: KING FAHD UNIVERSITY OF PETROLEUM AND MINERALS, Dhahran (SA); Imam Abdulrahman Bin Faisal University, Dammam (SA)

(72) Inventors: Mohammad A. Gondal, Dhahran (SA); Munirah Abdullah Al-Messiere, Dammam (SA); Firdos Alam Khan, Dammam (SA); Suriya Rehman, Dammam (SA); Abdulhadi Baykal, Dammam (SA); Reem Khalid Al-Dakheel, Dammam (SA)

(73) Assignees: KING FAHD UNIVERSITY OF PETROLEUM AND MINERALS, Dhahran (SA); Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 17/535,081

(22) Filed: Nov. 24, 2021

(65) Prior Publication Data
US 2022/0163453 A1 May 26, 2022

Related U.S. Application Data

(60) Provisional application No. 63/118,443, filed on Nov. 25, 2020.

(51) Int. Cl.
*G01N 21/71* (2006.01)
*G01N 33/00* (2006.01)
*G01N 1/28* (2006.01)

(52) U.S. Cl.
CPC .......... *G01N 21/718* (2013.01); *G01N 1/286* (2013.01); *G01N 33/0098* (2013.01); *G01N 2001/2866* (2013.01); *G01N 2201/06113* (2013.01)

(58) Field of Classification Search
CPC ... G01J 3/443; G01N 33/0098; G01N 21/718; G01N 2001/2866
See application file for complete search history.

(56) References Cited

U.S. PATENT DOCUMENTS

2005/0200843 A1 9/2005 Kumar et al.
2007/0218556 A1 9/2007 Harris et al.

FOREIGN PATENT DOCUMENTS

| CN | 204214779 U | 3/2015 |
| CN | 105044050 A | 11/2015 |
| CN | 104374753 B | 9/2016 |

OTHER PUBLICATIONS

Apr. 22, 2020, Wangcharoen, "Antioxidant activity changes during hot-air drying of Moringa oleifera leaves", Maejo Int. J. Sci. Technol. 2013 (Year: 2013).*

(Continued)

*Primary Examiner* — Maurice C Smith
(74) *Attorney, Agent, or Firm* — Oblon, McClelland, Maier & Neustadt, L.L.P.

(57) ABSTRACT

Method for quantifying the micronutrient profile of *Moringa oleifera* tree leaves (MOLs) using calibration free laser induced breakdown spectroscopy (CF-LIBS).

20 Claims, 28 Drawing Sheets

(56) References Cited

OTHER PUBLICATIONS

Aldakheel, et al. ; Bactericidal and In Vitro Cytotoxicity of Moringa oleifera Seed Extract and Its Elemental Analysis Using Laser-Induced Breakdown Spectroscopy ; MDPI pharmaceuticals ; Aug. 13, 2020 ; 18 Pages.

Mehta, et al. ; Role of Spectral Studies in Detection of Antibacterial Phytoelements and Phytochemicals of Moringa oleifera ; Food Biophysics 6 ; pp. 497-502 ; 2011 ; Abstract Only ; 9 Pages.

Umar, et al. ; Determination of Micronutrients and Toxic Elements in Moringa Oleifera Leaves by Calibration Free Laser-Induced Breakdown Spectroscopy (LIBS) ; Taylor Francis Online ; Abstract Only ; 6 Pages.

Watal, et al. ; LIBS-Based Detection of Antioxidant Elements: A New Strategy ; Advanced Protocols in Oxidative Stress II ; pp. 275-285 ; Sep. 30, 2009 ; Abstract Only ; 6 Pages.

Aldakheel, et al. ; Spectral analysis of Miracle Moringa tree leaves using X-ray photoelectron, laser induced breakdown and inductively coupled plasma-optical emission spectroscopic techniques; Talanta ; Apr. 17, 2020 ; 11 Pages.

\* cited by examiner

QUANTIFICATION OF THE MICRONUTRIENT PROFILE IN *MORINGA OLEIFERA* TREE LEAVES USING CALIBRATION FREE LASER INDUCED BREAKDOWN SPECTROSCOPY

STATEMENT OF PRIOR DISCLOSURE BY THE INVENTOR

Aspects of the present disclosure are described in R. K. Aldakheel, M. A. Gondal, M. M. Nasr, M. A. Almessiere, N. Idris.; "Spectral analysis of Miracle Moringa tree leaves using X-ray photoelectron, laser induced breakdown and inductively coupled plasma-optical emission spectroscopic techniques"; 2020; Talanta; 217: 121062. incorporated herein by reference in its entirety.

BACKGROUND OF THE INVENTION

Technical Field

The present disclosure is directed to a method of analyzing the micronutrient profile of *Moringa oleifera* leaves with calibration free laser induced breakdown spectroscopy and comparing the results with standard methods of determining micronutrient contents.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted The use of medicinal plants for human health is well-known. The micronutrients present in medicinal plants can play a vital role in many pharmacological and therapeutic applications. Micronutrients are can be categorized into two groups, which include but are not limited to, the major elements, calcium (Ca), chlorine (Cl), phosphorus (P), potassium (K), sodium (Na), sulfur (S), and magnesium (Mg), and trace elements, iodine (I), iron (Fe), Zinc (Zn), Selenium (Se), chromium (Cr), copper (Cu), molybdenum (Mo), and manganese (Mn). To preserve human health, an essential amount of these major and trace elements is required. See Y. Alresawum, H. Ghalila, S. Lahmar, A. V. Gholap Yvon, G. M. Kongbonga, W. M. Feudjio, Laser Induced Breakdown Spectroscopy (LIBS) for Minerals Analysis and for Monitoring the Change in Elemental Compositions of the Mixtures of Herbal Medicines, Chem. Mater. 9 (2017) 68-76, incorporated herein by reference in their entirety.

*Moringa oleifera* (MO), commonly called the drumstick tree, is known to have medicinal properties. In Asia, some parts of this plant are used to make traditional medicine for diabetes treatment, and antimicrobial, and pharmacological applications. See B. Padayachee, H. Baijnath, An updated comprehensive review of the medicinal, phytochemical and pharmacological properties of *Moringa oleifera*, S. Afr. J. Bot. 2019, each incorporated herein by reference in their entirety. The major elements and nutrients in the *Moringa oleifera* leaves (MOLs) make them beneficial as the supplements and growth promoters. See R. Lakshminarayana, M. Raju, T. P. Krishnakantha, V. Baskaran, Determination of major carotenoids in a few Indian leafy vegetables by high-performance liquid chromatography, J. Agric. Food Chem. 53 (2005) 2838-2842; and M. D. I. Sanchez, C. J. Lopez, N. J. R. Vazquez, High-performance liquid chromatography method to measure α- and β-tocopherol in leaves, flowers and fresh beans from *Moringa oleifera*, J. Chromatogr. A 1105 (2006) 111-114, each incorporated herein by reference in their entirety.

Despite some traditional applications, the bioactivity and biocompatibility of the MOLs in terms of their elemental compositions and micronutrient qualities are not clearly understood. Inductively coupled plasma atomic emission spectroscopy (ICP-OES), graphite furnace atomic absorption spectroscopy (GF-AAS), X-ray photoelectron spectroscopy and mass spectrometry (MS) have recently been used to determine the elemental compositions of various medicinal plants. See S. M. Enamorado-Baez, J. M. Abril, J. M. Gomez-Guzman, Determination of 25 trace element concentrations in biological reference materials by ICP-MS following different microwave assisted acid digestion methods based on scaling masses of digested samples, Anal. Chem. 851713 (2013)1-4; A. Maida, A. Farooq, N. Raziya, R. Umer, T. Kazi, M. Nadeem, Mineral composition of *Moringa oleifera* leaves and pods from different regions of Punjab, Pakistan, Asian J. Plant Sci. 4 (2005) 417-421, each incorporated herein by reference in their entirety. However, these spectroscopic techniques are both time consuming in terms of the complex sample preparation protocols, suffer from the chances of sample contamination and may not detect every element present in the sample. See S. Sharma, N. Shukla, A. S. Bharti, K. N. Uttam, Simultaneous Multi-elemental Analysis of the Leaf of *Moringa oleifera* by Direct Current Arc Optical Emission Spectroscopy, Natl. Acad. Sci. Lett 41(2018) 65-68, incorporated herein by reference in its entirety. To surmount these shortcomings, an accurate method for identifying and evaluating the elemental compositions of medicinal plants including *Moringa oleifera* is necessary.

Laser induced breakdown spectroscopy (LIBS) is a powerful, non-destructive, and multi-elemental analytical technique for all types and phases of materials without any complex sample preparation procedures. See M. A. Gondal, M. N. Siddiqui, M. M. Nasr, Detection of trace metals in asphaltenes using an advanced laser-induced breakdown spectroscopy (LIBS) technique, Energ. Fuel. 24 (2010) 1099-1105; and M. A. Gondal, Z. S. Seddigi, M. M. Nasr, B. Gondal, Spectroscopic detection of health hazardous contaminants in lipstick using Laser induced breakdown spectroscopy, J. Hazard. Mater. 175 (2010) 726-732, each incorporated herein by reference in their entirety. Over the years, LIBS has been used for both qualitative and quantitative elemental analysis of various materials. See A. El-Hussein, A. K. Kassem, H. Ismail, M. A. Harith, Exploiting LIBS as a spectrochemical analytical technique in diagnosis of some types of human malignancies, Talanta 82 (2010) 495-501; M. A. Almessiere, R. Altuwiriqi, M. A. Gondal, R. K. AL-Dakheel, H. F. Alotaibi, Qualitative and quantitative analysis of human nails to find correlation between nutrients and vitamin D deficiency using LIBS and ICP-AES, Talanta 185 (2018) 61-70; and S. Mehta, P. Kumar Rai, N. Kumar Rai, A. K. Rai, D. Bicanic, G. Watal, Role of Spectral Studies in Detection of Antibacterial Phytoelements and Phytochemicals of *Moringa oleifera*, Food Biophys. 6 (2011) 497-502, US20190170617, each incorporated herein by reference in their entirety. Each of the aforementioned methods of determining the elemental composition of *Moringa oleifera* leaves suffers from one or more drawbacks hindering their adoption. Accordingly, it is one object of the present disclosure to provide faster detection and simplified sample preparation methods to determine the quantity of micronutrients and micronutrient profile in *Moringa oleifera* leaves.

BRIEF SUMMARY OF THE INVENTION

In one aspect the present disclosure includes a method of determining the micronutrient profile of *Moringa oleifera* leaves by drying the *Moringa oleifera* leaf to form a dried leaf;

grinding the dried leaf to form a homogeneous mixture; compressing the homogeneous mixture into a pellet comprising a chromophore; analyzing the elemental composition of the pellet with calibration free laser-induced breakdown spectroscopy (CF-LIBS);

wherein the analyzing is carried out with a CF-LIBS algorithm configured to calculate the quantity of a plurality of elements selected from the group Ca, Cu, Fe, K, Mg, Mn, Na, P, S, and Zn present in the dried leaf pellets; and wherein the CF-LIBS is performed using a pulsed laser having a pulse width of 5 to 10 ns, a repetition rate of 15 to 25 Hz, a time delay of 290 to 350 ns, and a laser energy of 10 to 30 mJ.

In some embodiments, the present invention provides a method for determining the concentration of a set of elements in an Nth sample of *Moringa oleifera* leaves using laser-induced breakdown spectroscopy to produce an Nth sample element profile, wherein the calculating comprises mixing variable amounts of the first through Nth samples to produce a composite dose comprising at least two of the first through Nth samples.

In some embodiments, the spectra of at least 2 laser pulses are accumulated to get the average CF-LIBS spectrum.

In some embodiments, the pellets are mounted on the top of a two-dimensional motorized translational stage during CF-LIBS analysis.

In some embodiments, the detected element during CF-LIBS analysis is Ca and at least one atomic line at 422.6, 445.4, 393.3 and 315.8 nm is monitored, and the optimum gated time delay of the pulsed laser is 300 ns.

In some embodiments, the detected element during CF-LIBS analysis is K and at least one atomic line at 404.7, 766.4, and 769.8 nm is monitored, and the optimum gated time delay of the pulsed laser is 332 ns.

In some embodiments, the detected element during CF-LIBS analysis is Cu and the atomic line at 324.7 nm is monitored.

In some embodiments, the detected element during CF-LIBS analysis is Fe and at least one atomic line at 248.3, 259.9, and 275.5 nm is monitored.

In some embodiments, the detected element during CF-LIBS analysis is Mg and at least one atomic line at 279.5, 280.2, and 285.2 nm is monitored.

In some embodiments, the detected element during CF-LIBS analysis is Mn and at least one atomic line at 403.0, 259.3, and 257.6 nm is monitored.

In some embodiments, the detected element during CF-LIBS analysis is Na and at least one atomic line at 328.5, 588.9, and 589.5 nm is monitored.

In some embodiments, the detected element during CF-LIBS analysis is P and at least one atomic line at 253.5 and 255.3 nm is monitored.

In some embodiments, the detected element during CF-LIBS analysis is S and at least one atomic line at 543.2 and 545.3 nm is monitored.

In some embodiments, the detected element during CF-LIBS analysis is Zn and at least one atomic line at 250.1, 255.7, and 334.5 nm is monitored.

In some embodiments, the sensitivity of the CF-LIBS measurement is sufficient to detect 1 mg/L of at least one of Ca, Cu, Fe, K, Mg, Mn, Na, P, S, and Zn in the pellets.

In some embodiments, the CF-LIBS algorithm assumes the sample is in local thermodynamic equilibrium (LTE) and LTE is determined by the number density of electrons and electron temperature in the plasma during the CF-LIBS measurements and the electron temperature is between 9,000 to 10,000 K and the number density of electrons is $0.10 \times 10^{16}$ to $0.50 \times 10^{17}$ cm$^{-3}$.

In some embodiments, the current method includes validating the micronutrient profile results of CF-LIBS by comparing to the standard method of elemental detection using ICP-OES wherein the relative accuracy is in the range of 0.01 to 0.50.

In some embodiments, the chromophore is a fused ring aromatic compound.

In some embodiments, the fused ring aromatic compound is selected from the group comprising substituted naphthalene, fluorene, and fluorenone derivatives.

In some embodiments, the chromophore is mixed into the homogeneous mixture before being compressed into a pellet and/or the chromophore is coated onto the side of the pellet onto which the laser will be focused.

The foregoing general description of the illustrative embodiments and the following detailed description thereof are merely exemplary aspects of the teachings of this disclosure and are not restrictive.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 4A:
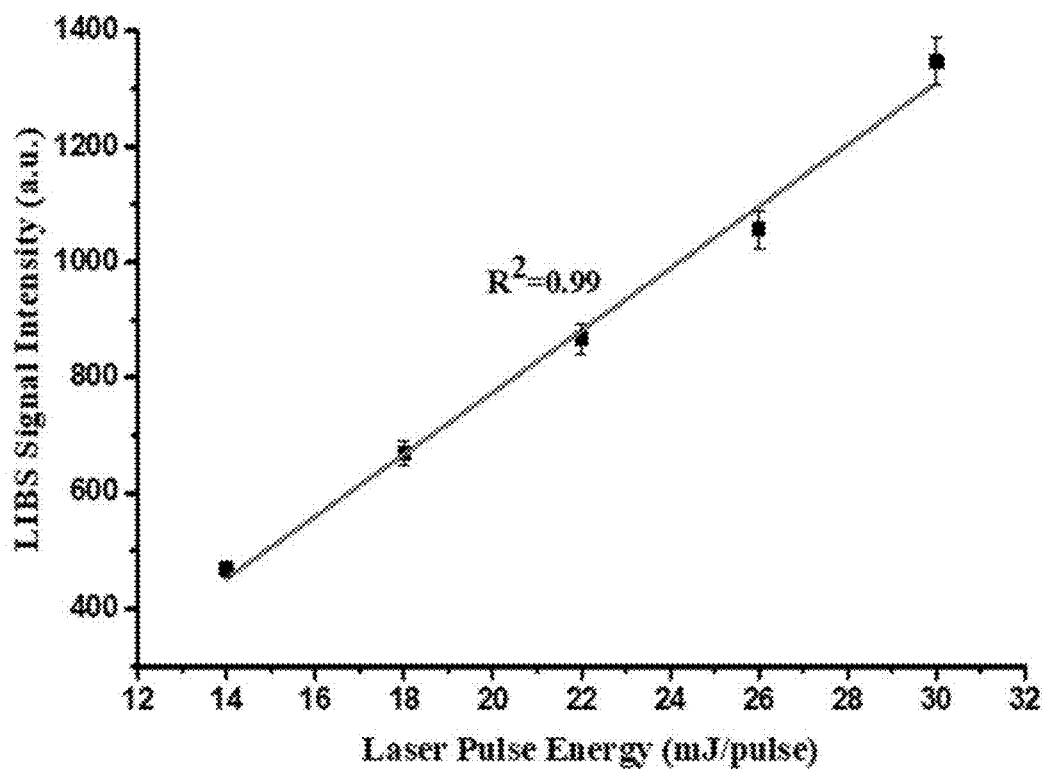
FIG. 4A illustrates the linear dependence of LIBS signal intensity on the incident laser pulse energy (14-30 mJ/pulse)
Figure 4B:
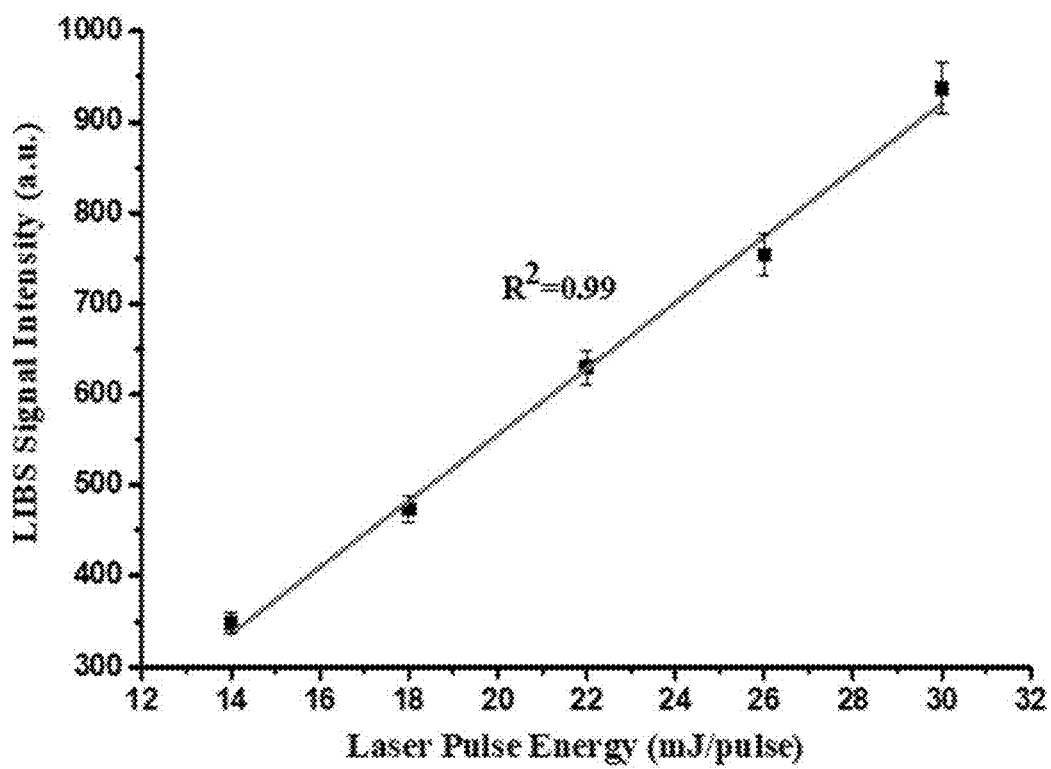
Figure 5:
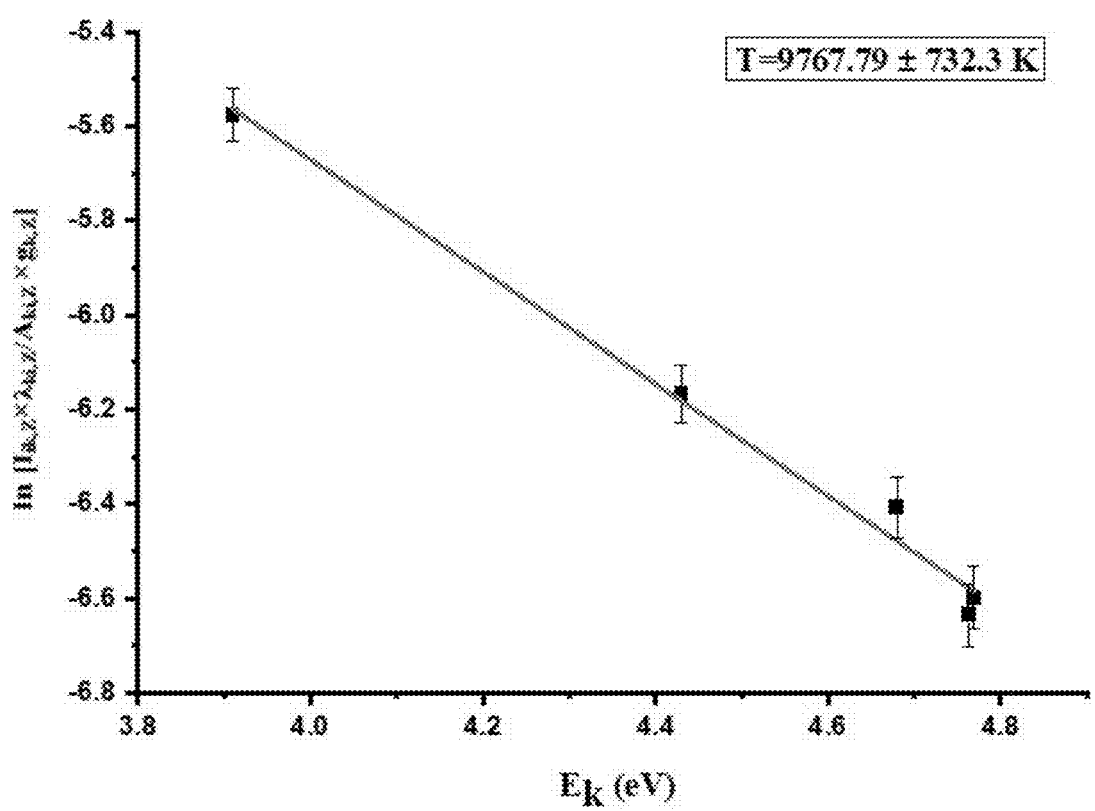
Figure 6:
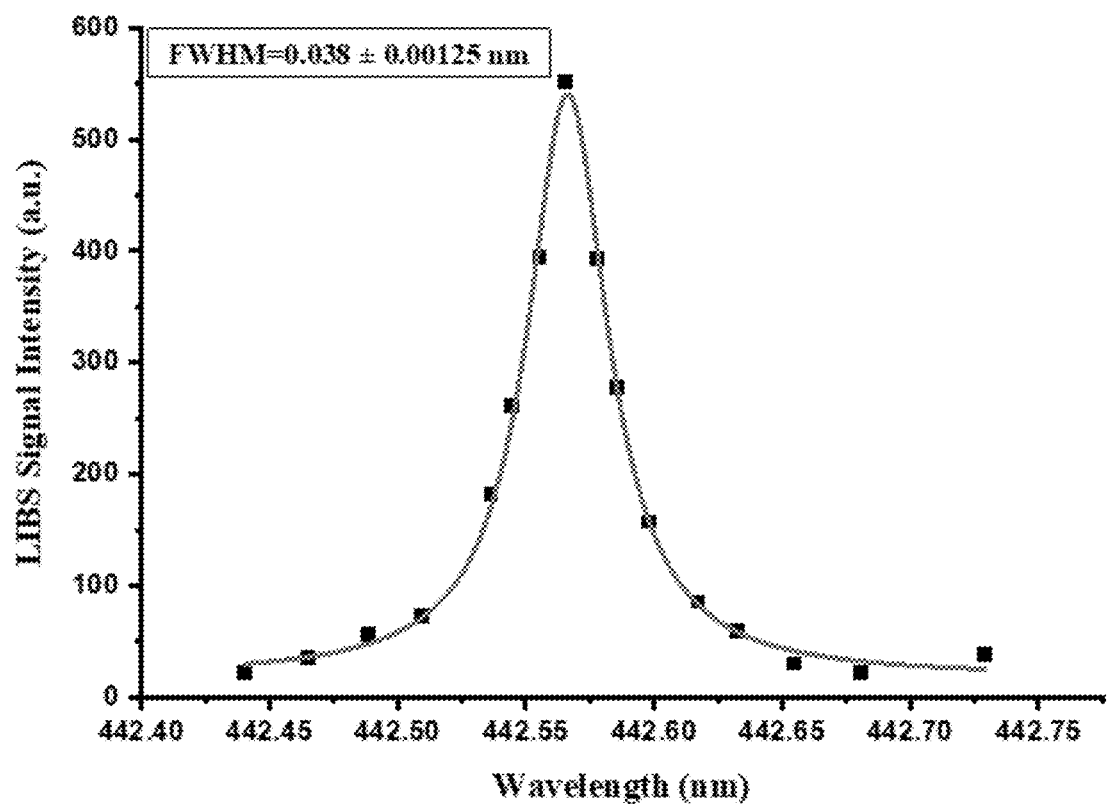
Figure 7A:
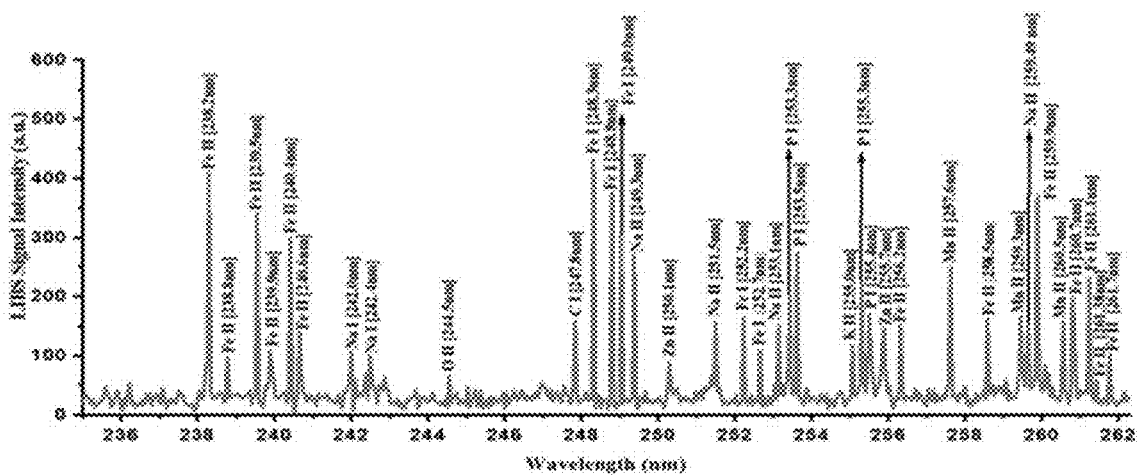
Figure 7B:
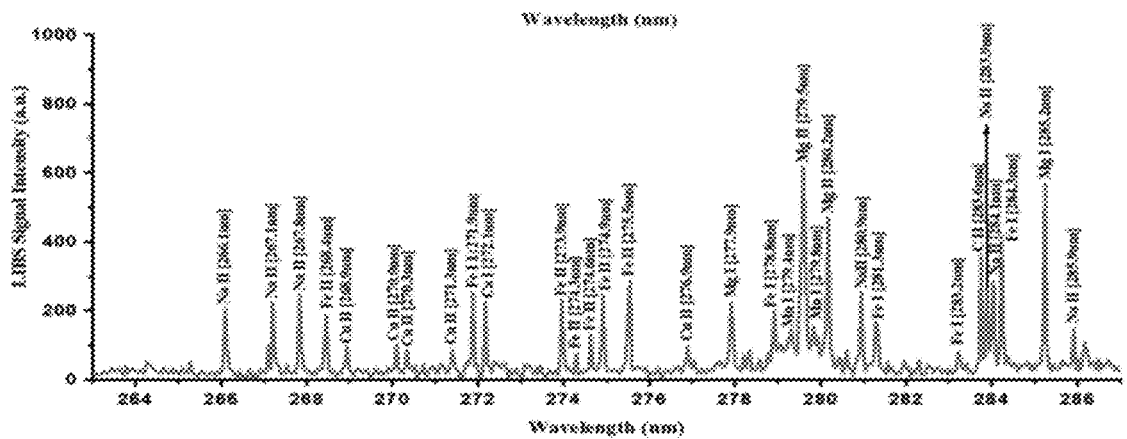
Figure 7C:
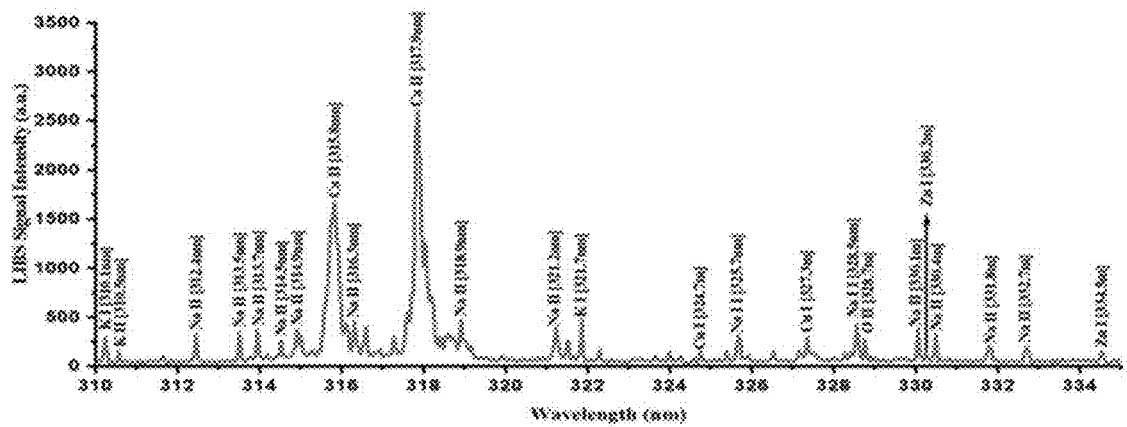
Figure 8A:
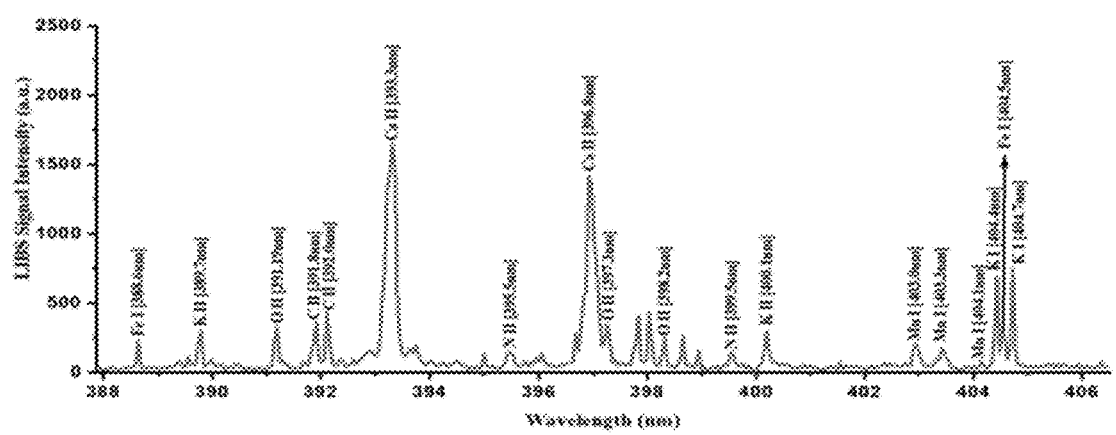
Figure 8B:
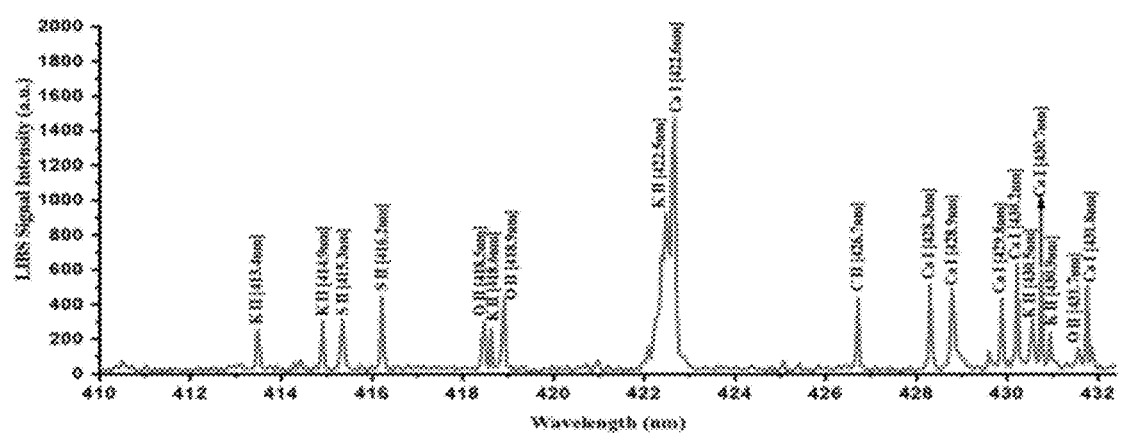
Figure 8C:
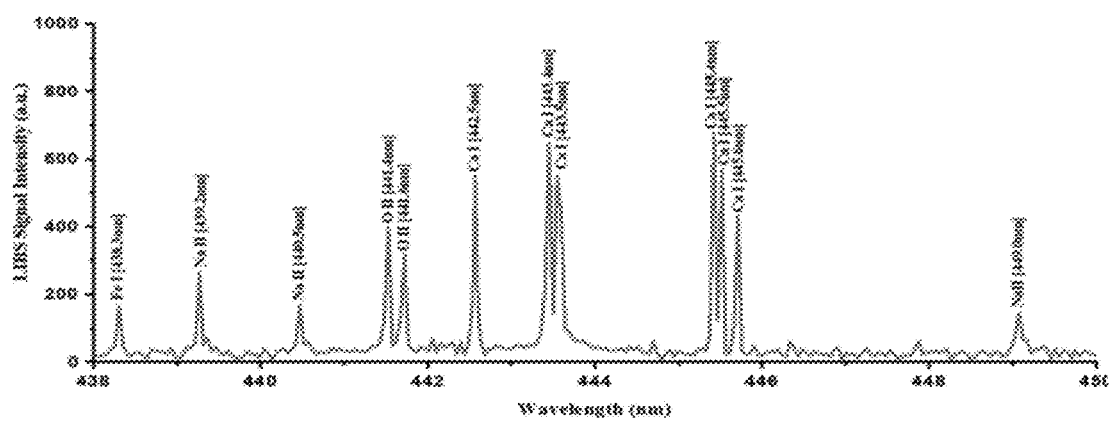
Figure 9A:
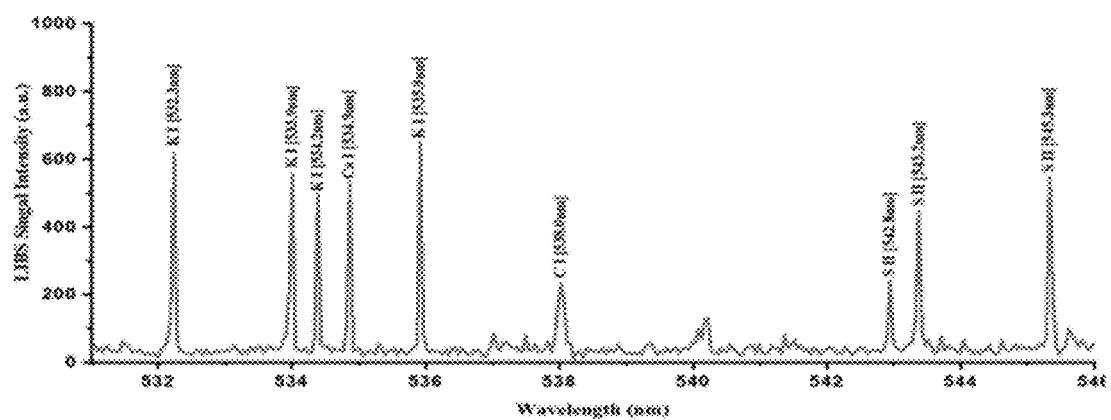
Figure 9B:
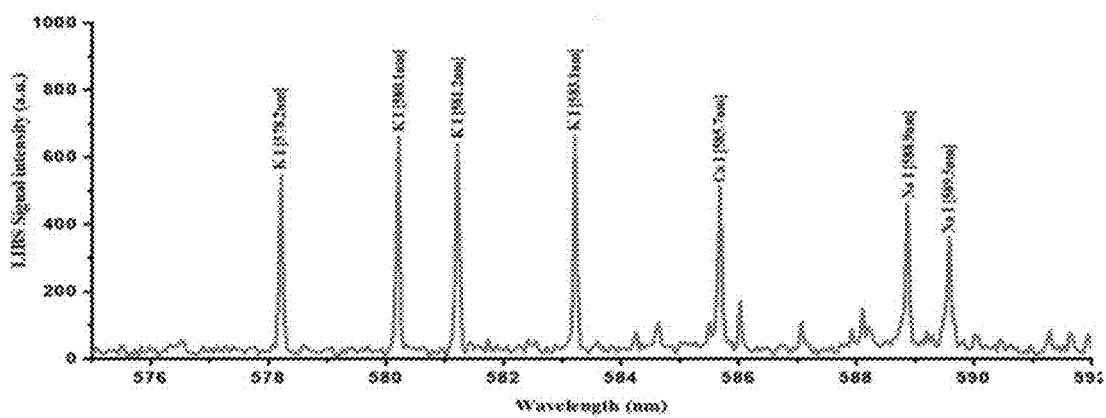
Figure 9C:
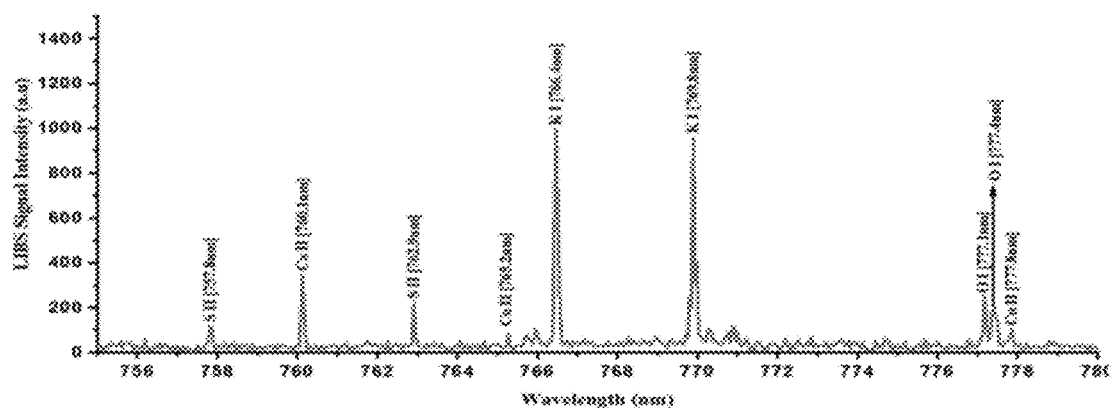
Figure 10A:
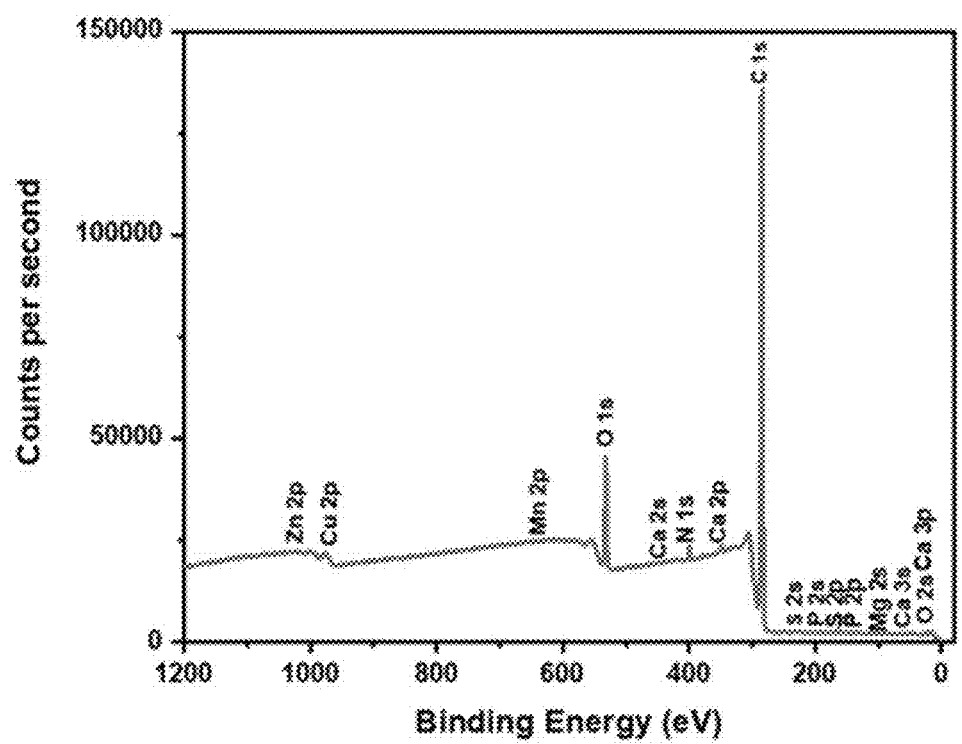
Figure 10B:
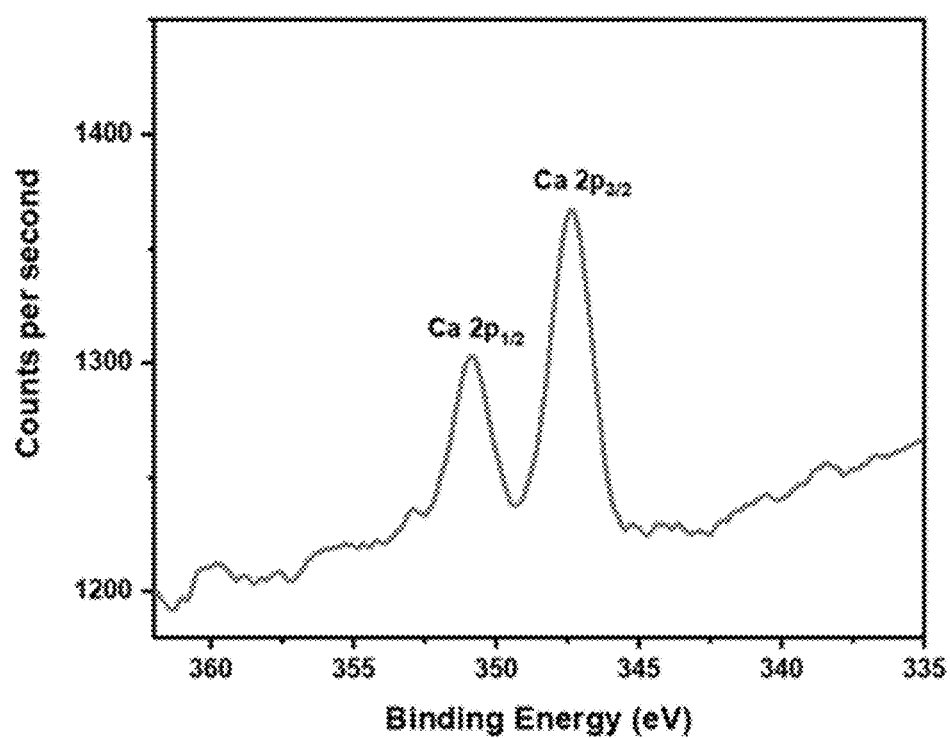
Figure 10C:
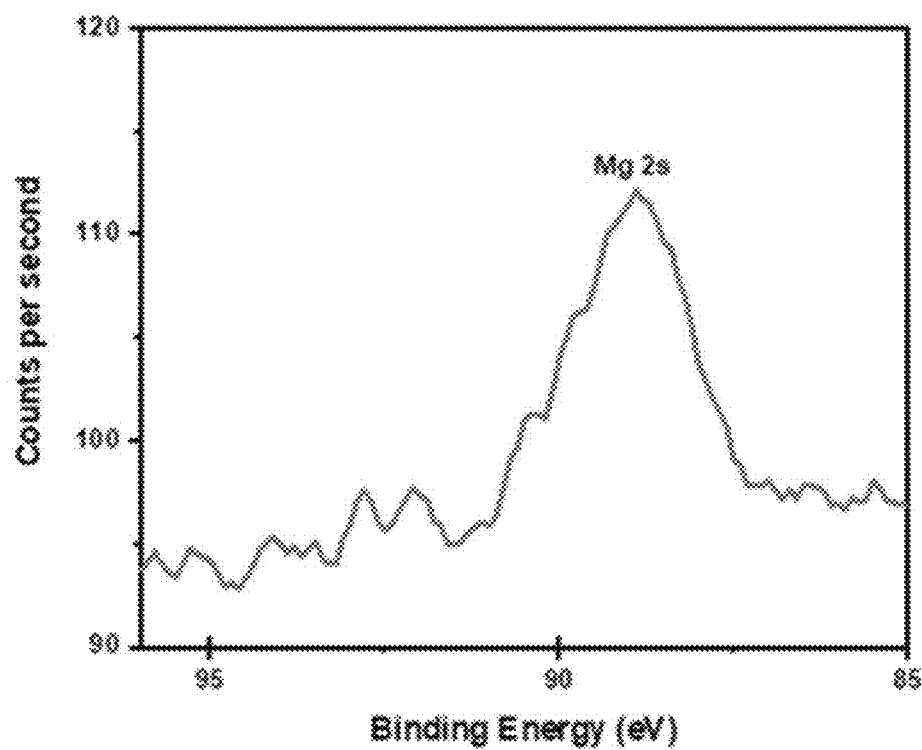
Figure 10D:
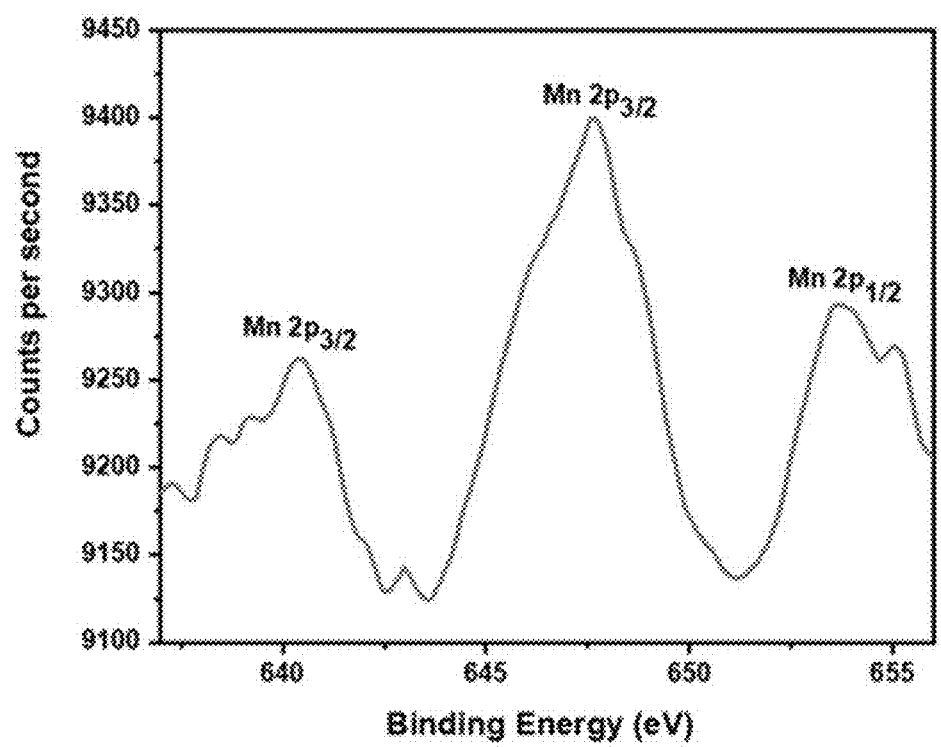
Figure 10E:
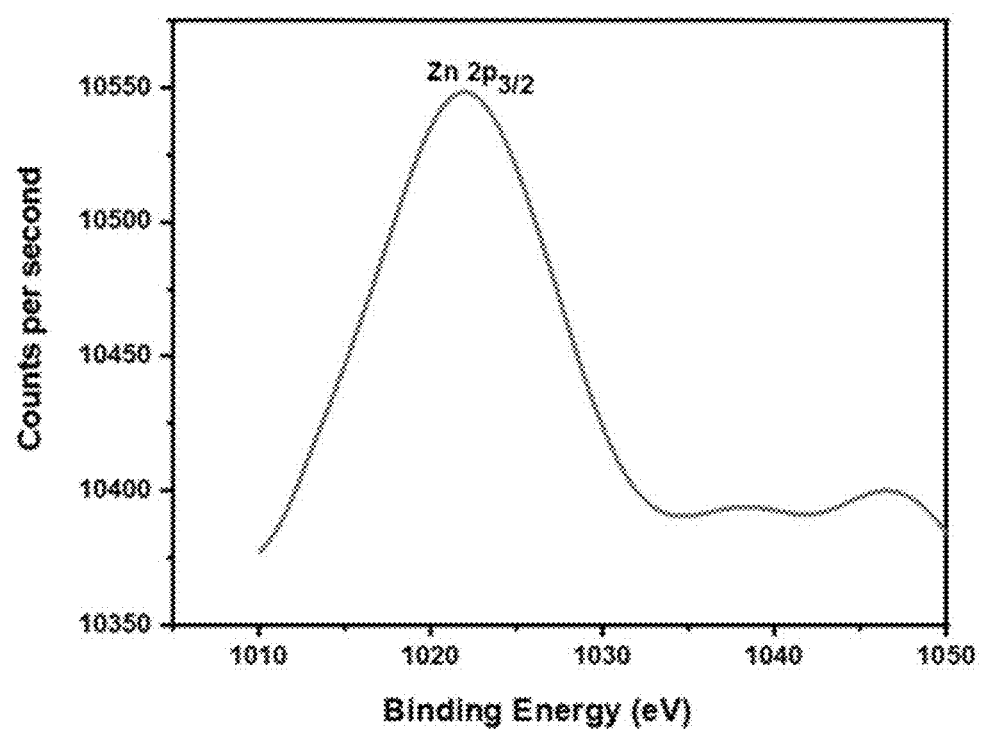
Figure 10F:
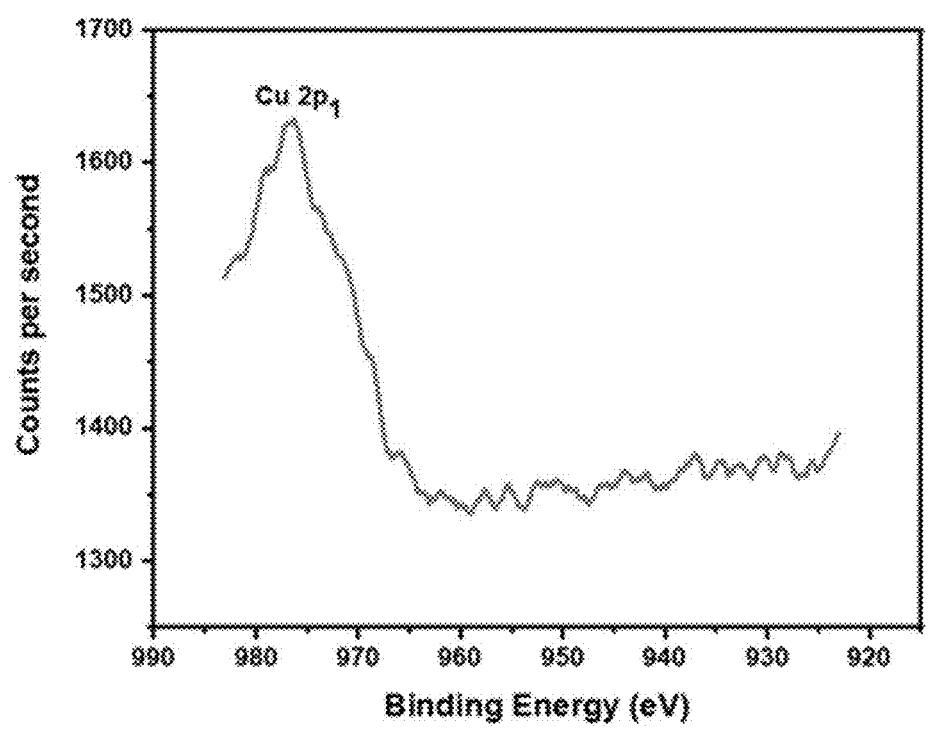
Figure 10G:
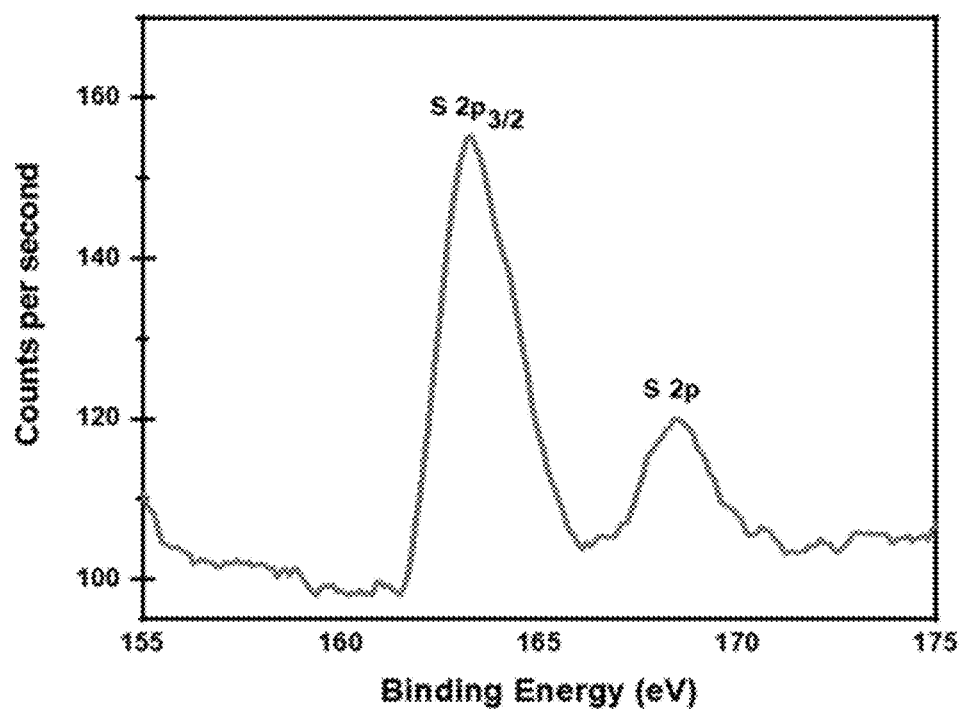
Figure 10H:
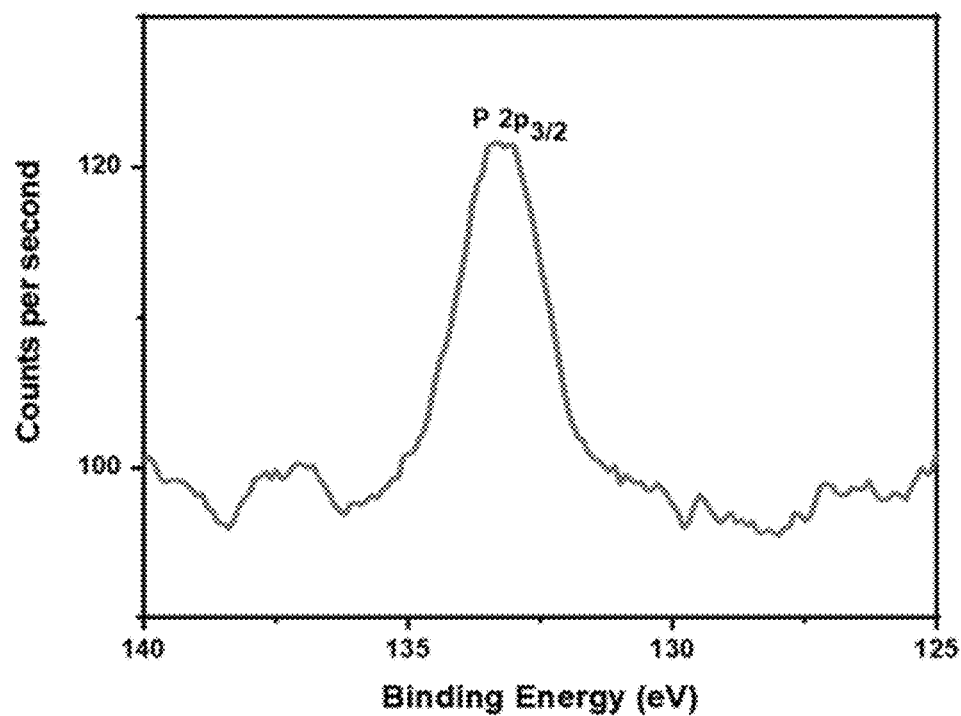
Figure 10I:
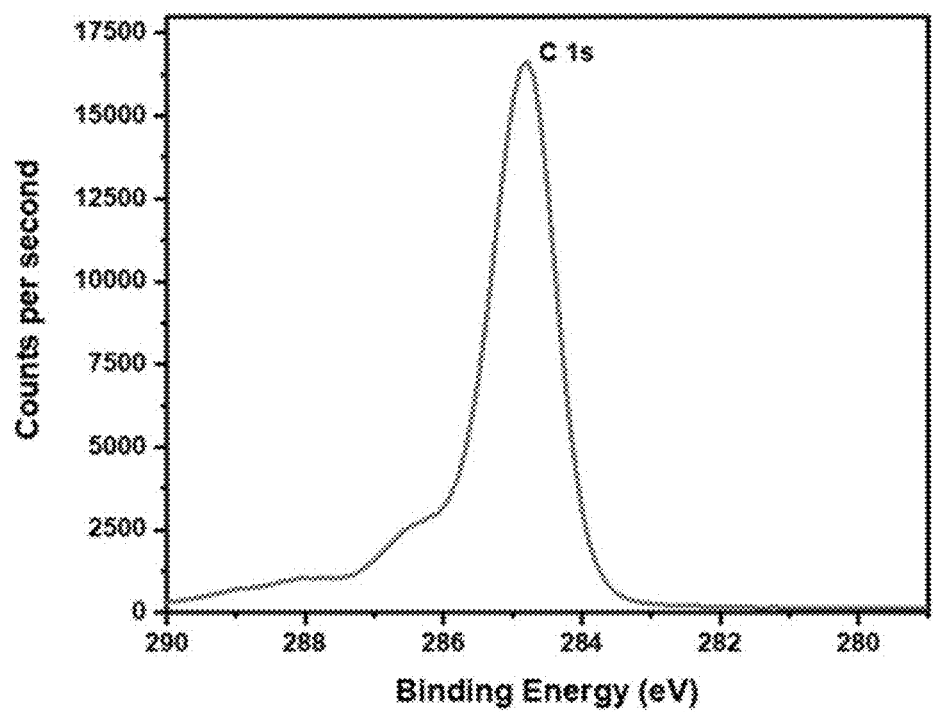

for the neutral atomic transition line of Ca I monitored at 422.6 nm for the MOL samples;

FIG. 4B illustrates the linear dependence of LIBS signal intensity on the incident laser pulse energy (14-30 mJ/pulse) for the neutral atomic transition line of K I monitored at 769.8 nm for the MOL samples;

FIG. 5 illustrates the Boltzmann plot for determining electron temperature in the plasma during the LIBS analysis, using the spectral emission lines of Ca I (429.89, 430.77, 442.54, 616.22, 649.38 nm). The temperature was found to be 9767.79±732.3 K for the MOL samples;

FIG. 6 illustrates the Stark-broadened profile of the peak neutral atomic transition line of Ca I, monitored at 442.5 nm, used to estimate the experimental value of the number density of electrons ($N_e$) present in the plasma during LIBS analysis. The FWHM of the plot was found to be 0.038±0.00125 nm, the value of $N_e$ thereby calculated to be ≈$0.31 \times 10^{17}$ $cm^{-3}$;

FIG. 7A illustrates a LIBS spectrum for the MOL samples in the range 235-262 nm. Elements detected in this range include Na, Fe, Cu, Ca, Mg, Mn, Zn, P, C, O, and K;

FIG. 7B illustrates a LIBS spectrum for the MOL samples in the range 262-286 nm. Elements detected in this range include Na, Fe, Cu, Ca, Mg, Mn, and C;

FIG. 7C illustrates a LIBS spectrum for the MOL samples in the range 310-335 nm. Elements detected in this range include Na, Cu, Ca, Zn, O, and K;

FIG. 8A illustrates a LIBS spectrum for the MOL samples in the range 388-406 nm. Elements detected in this range include Fe, O, C, Ca, N, Mn, and K;

FIG. 8B illustrates a LIBS spectrum for the MOL samples in the range 410-432 nm. Elements detected in this range include Ca, C, S, O and K;

FIG. 8C illustrates a LIBS spectrum for the MOL samples in the range 438-450 nm. Elements detected in this range include Fe, Na, O, and Ca;

FIG. 9A illustrates a LIBS spectrum for the MOL samples in the range 531-546 nm. Elements detected in this range include K, Ca, C, and S;

FIG. 9B illustrates a LIBS spectrum for the MOL samples in the range 575-592 nm. Elements detected in this range include K, Ca, and Na;

FIG. 9C illustrates a LIBS spectrum for the MOL samples in the range 755-780 nm. Elements detected in this range include S, Ca, S, Cu, K, and O;

FIG. 10A illustrates a XPS spectrum for the MOL samples in the binding energy range 1200-0 eV. Elements detected in this range include Zn, Cu, Mn, O, Ca, N, Ca, C, S, P, and Mg;

FIG. 10B illustrates a XPS spectrum for the MOL samples in the binding energy range 365-335 eV. The element detected in this range is Ca;

FIG. 10C illustrates a XPS spectrum for the MOL samples in the binding energy range 100-85 eV. The element detected in this range is Mg;

FIG. 10D illustrates a XPS spectrum for the MOL samples in the binding energy range 635-655 eV. The element detected in this range is Mn;

FIG. 10E illustrates a XPS spectrum for the MOL samples in the binding energy range 1005-1050 eV. The element detected in this range is Zn;

FIG. 10F illustrates a XPS spectrum for the MOL samples in the binding energy range 990-920 eV. The element detected in this range is Cu;

FIG. 10G illustrates a XPS spectrum for the MOL samples in the binding energy range 155-175 eV. The element detected in this range is S;

FIG. 10H illustrates a XPS spectrum for the MOL samples in the binding energy range 140-125 eV. The element detected in this range is P;

FIG. 10I illustrates a XPS spectrum for the MOL samples in the binding energy range 290-275 eV. The element detected in this range is C;

DETAILED DESCRIPTION

Embodiments of the present disclosure will now be described more fully hereinafter with reference to the accompanying drawings, in which some, but not all embodiments of the disclosure are shown.

Micronutrient profile is characterized as the presence and relative quantities of a plurality of elements selected from the following Ca, Cu, Fe, K, Mg, Mn, Na, P, S, and Zn, in a sample.

In some embodiments, the *Moringa oleifera* leaves are obtained, for example through purchase at a market or for example taken from a *Moringa oleifera* tree. The leaves are then dried in an oven at less than 100° C. The dried leaves are then ground into a homogenous powder which can be achieved manually, for example using a mortar and pestle, or mechanically for example using a grinder or shredder. At least a portion of the homogenous powder is then compressed into a sample pellet for example using a hydraulic laboratory pellet press. The pellet contains a front-side on which the laser will focus during LIBS analysis.

In some embodiments, the pellet also comprises a chromophore either mixed into the homogeneous mixture of MOLs and/or coated on the front-side of the pellet. The chromophore attenuates the LIBS laser excitation pulse thereby preventing signal distortion from effects described in the examples below.

LIBS

The LIBS technique employs a high-power pulsed laser focused on a small spot of the test sample. This generates high temperature ionized plasma (comprised of the electronic and ionic excited states) due to the interaction of the laser pulse with the sample. Next, light is emitted through radiative energy transfer and is detected in the form of indexed emission lines from the specific elements present in the test sample. LIBS can analyze samples in any state, however it is disclosed herein that for organic solid samples the parameters need to be within particular ranges in order to obtain accurate results. This technique, unlike XPS and ICP, can detect all elements and is only limited by the power of the laser and the detector. In general LIBS measurements require a matrix of similar composition to the sample to evaluate the relative abundance of each constituent element. This requirement prevents the analysis of organic compounds with unknown composition; therefore, calibration free LIBS (CF-LIBS) is preferably employed.

This method of using CF-LIBS to quantify the micronutrient composition and profile in *Moringa oleifera* leaves reduces the need for laborious sample preparation compared to other methods. CF-LIBS can determine the presence of multiple elements and the quantification of these elements is based on the measurement of line intensities and properties of the plasma, including plasma number density of electrons and temperature. CF-LIBS also assumes a Boltzmann distribution of excited states, which does not require the use of calibration curves or the use of a matrix with a matched composition to the sample, therefore CF-LIBS can analyze samples that have not previously been characterized. The requirement of a matrix, especially for organic plant material, is difficult because obtaining a sample matrix similar to that of the unknown sample matrix is near impossible. As shown in the examples below, based on the relative intensities of spectral lines, a Boltzmann plot is constructed. The elemental concentrations can then be calculated from the y-intercepts of the lines. To ensure accuracy of CF-LIBS results the plasma must be in local thermodynamic equilibrium, and optically thin. By ensuring optimal sample and laser conditions this set of conditions could potentially be used to determine the micronutrient profile of other plant based organic material.

Sensitivity

The detection limit of LIBS is based on properties such as, plasma temperature, detection window, and the strength of the transition line. The current method allows for sensitive detection of micronutrients in plant material as low as 1 mg/L. Micronutrient concentration is measured based on the weight or mass of plant matter, however, in some alternative embodiments, a concentration may be measured based on volume of the micronutrient and plant matter. The sensitivity is based on the rate of plasma generation of the material in LIBS analysis and the amount of micronutrient present in the standard sample per unit volume.

As shown by the following examples a number of *Moringa oleifera* leaves were formed into pellets and analyzed for their micronutrient composition. The analysis was performed using a LIBS setup and a quantity of micronutrients such as, but not limited to, calcium, potassium, and magnesium was detected in the leaves. In some embodiments, these results were then counter-verified using standard techniques, such as XPS and ICP-OES. The micronutrient quantities in the leaves were estimated using CF-LIBS and were in accordance with the results obtained by the standard ICP-OES technique. The accuracy of the CF-LIBS measurement shows that this method can be used to determine the micronutrient profile of organic plant-based material.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

EXAMPLES

LIBS Setup

Figure 1:
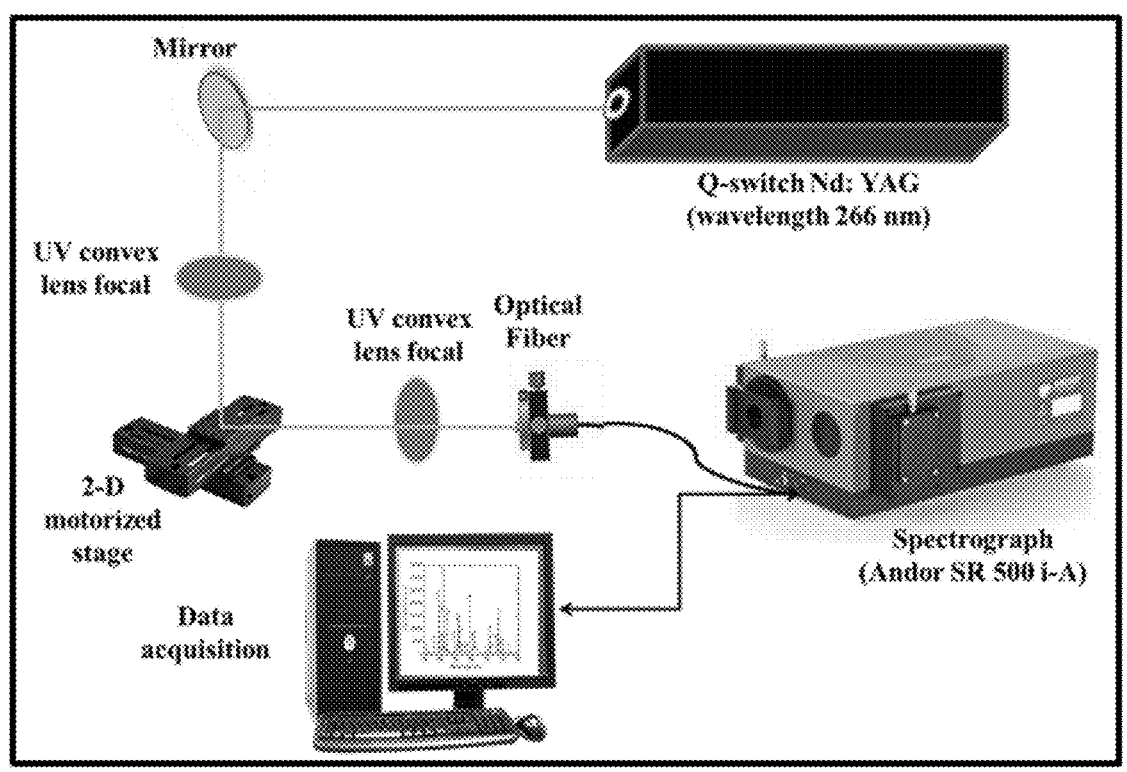
FIG. 1 illustrates the schematic diagram of the laser induced breakdown spectroscopy (LIBS) setup. An ultraviolet (UV) Q-switch pulsed Nd:YAG laser (model QUV-266-5 operated at the fourth-harmonic generation mode of wavelength 266 nm) with pulse width of 8 ns, repetition rate of 20 Hz and maximum output energy of 50 mJ was utilized to excite the samples.

The description of the LIBS setup is described here and incorporated by reference. See Gondal et al., Spectroscopic detection of health hazardous contaminants in lipstick using Laser induced breakdown spectroscopy (2010); El-Hussein et al.; and Almessiere et al. FIG. 1 shows the LIBS setup that was used to measure the contents of the trace and major elements in the proposed MOL samples. An ultraviolet (UV) Q-switch pulsed Nd:YAG laser (model QUV-266-5 operated at the fourth-harmonic generation mode of wavelength 266 nm) with pulse width of 8 ns, repetition rate of 20 Hz and maximum output energy of 50 mJ was utilized to excite the samples. The laser beam was collimated with a spot diameter of approximately 0.1 mm and focused onto the sample placed on a two-dimensional motorized stage to prevent damaging the sample and allow for movement in the X-Y direction.

The plasma emission signals were collected using a collimating miniature lens, which was interfaced with an optical fiber and placed at an angle of 45° with respect to the normal of the target sample. The optical fiber was connected to an optical spectrograph to disperse the plasma emission. A high-resolution 500 mm spectrograph (Andor SR 500i-A) with a grating groove density of 1199 lines/mm was used to provide effectively resolved spectral lines. The spectrograph covers a broad spectral wavelength range of 200, 300, 400, 500, 600, 700, 800 to 900 nm (ultraviolet, visible, and near-IR regions).

An intensified charge-coupled device camera (ICCD, model iStar 320T, 690×255 pixels) enabled the collection of the spectrum from the spectrograph, and directly converted that spectral (analogue) signal into a digital one. The ICCD camera is a fully integrated device comprising a high-performance digital delay generator, high-speed operated gate (or shutter), and highly sensitive camera unit. This delay generator, which is a time controller for the camera gating, was synchronized with the laser pulse. This systematic mechanism needed to be accomplished for a certain time delay, and yielded improvement in the signal-to-noise ratio (SNR) by reducing the strong background continuum plasma emissions.

Bremsstrahlung radiation, which mainly contributes to the background continuum emissions, occurs as a result of the deceleration of high-speed free electrons as they pass near a positively charged ion because of the strong electric (attractive) forces between them.

A dedicated software package (Andor SOLIS for Time Resolved: ICCD-3909) for the ICCD camera system was provided by the manufacturer. The digital signal was analyzed by the software, following which the spectrum was ready to be recorded on a PC monitor.

Samples Preparation for LIBS Analysis

Figure 2A:
FIG. 2A illustrates dry *Moringa oleifera* leaves (MOLs)
Figure 2B:
FIG. 2B illustrates MOLs ground into powder.
Figure 2C:
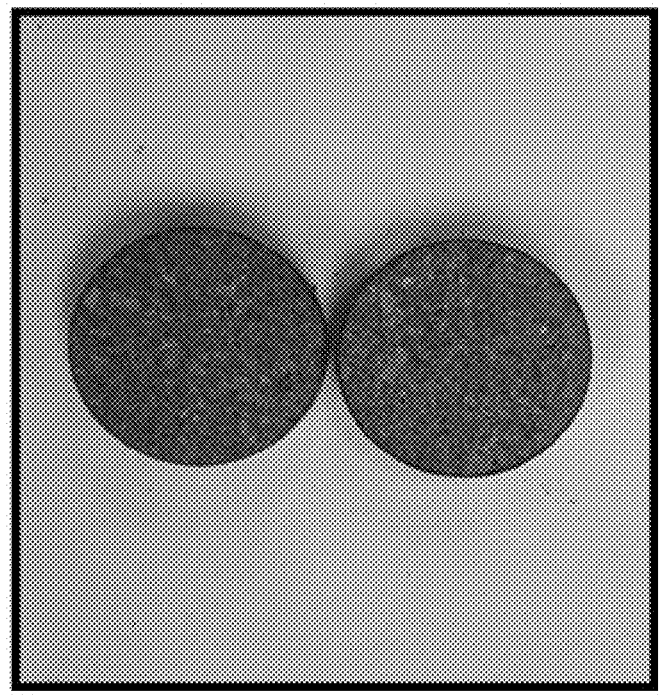
FIG. 2C illustrates MOLs formed into pellets.

Fresh, dry MOLs were purchased from a local market to prepare the samples. First, the MOLs were cleaned, ground, homogeneously mixed and compressed into pellets. Next, each pellet was directly loaded onto a sample holder for the spectroscopic analyses (FIG. 2). For LIBS analyses, each sample was placed on the top of a two-dimensional motorized translational stage. This sample preparation method was less inhibitive than that for other methods such as ICP and XPS described below.

Digestion Procedure of Samples for ICP-OES Analysis

The total elemental content in the dry MOL powder was determined using standard ICP-OES (ICP-OES Agilent model 5110) equipped with the Synchronous Vertical Dual View (SVDV) configuration. The trace elements present in the dry MOLs were quantified, these included the Ca, K, S, Na, Mg, P, Fe, Mn, Zn, Cu, Cr, and Se. In addition, the contents of metals and sulfur in the MOL samples were evaluated using the microwave (MW) assisted digestion method (Model EPA3052B). Approximately 100 mg of the MOL powder was digested in the Ultrawave Single Reaction Chamber (SRC) using the MW Digestion System (Milestone Inc.). In this process, a solution made from the concentrated nitric acid ($HNO_3$, Sigma Aldrich) (5 mL) and hydrogen peroxide ($H_2O_2$ 30% w/v, VWR International) (0.5 mL) was poured in sealed polytetrafluoroethylene MW-vessels. The samples were heated in three successive steps 1) 130° C. for 10 min, 2) 240° C. for 10 min, and 3) 240° C. for 15 min at a fixed power of 1500 W. The maximum pressure attained during the digestion was 130 bar. After completing the digestion process, the resultant samples were cooled for 15 min before being transferred to a polypropylene volumetric vial and diluted with 20 mL of de-ionized water. Meanwhile, the reagent blank sample was also prepared. The ICP-OES analysis of the samples was performed following the standard (method #200.7) set by the U.S. Environmental Protection Agency (EPA) hereby incorporated in its entirety.

ICP-OES Analysis of Dry MOL Pellets

ICP-OES was utilized to support LIBS results of the dry MOLs. The ICP-OES measurement was performed on the digested MOLs prepared using the MW assisted method. The ICP-OES spectra of the MOLs reaffirmed the existence of all the essential elements identified using LIBS measurement. The concentration of the Ca, Na, K, Fe, Mg, Mn, Cu, P, S and Zn in the MOLs were found to be 21817, 1072, 14268, 696, 4440, 81, 12, 2800, 8336 and 29 mg/L, respectively. Yet again, the contents of the Ca, K, Mg, P, and S in the MOLs were more than the other elements as shown by the ICP-OES analyses, indicating the nutritional and medicinal traits of the MO plant. Table 2 shows the measured elemental contents in the MOLs obtained using the standard ICP-OES technique. In short, the ICP results for the elemental composition in the MOLs were found to be consistent with LIBS outcomes.

XPS Analysis of Dry MOL Pellets

XPS analyses were performed using a Kratos Axis Ultra DLD instrument equipped with a monochromatic Al K$\alpha$ X-ray source of energy 1486.6 eV (operated at 150 W, multi-channel plate and delay line detector under the vacuum of approximately $10^{-9}$ mbar) to detect the valence states of the elements present in the dry MOLs. An aperture slot of dimension 300 μm×700 μm was used to record the XPS spectra (FIG. 10). The survey scan was performed using the pass energy of 160 eV at a step size of 1 eV. Meanwhile, the high-resolution spectra were recorded using the pass energy of 20 eV at a step size of 0.1 eV. To achieve complete charge neutralization by avoiding the differential charging effects, all the samples of dry MOLs were mounted on a floating mode. The binding energies of the elements present in the MOLs were adjusted by fixing C1s peak at 284.8 eV (FIG. 10A). FIG. 10A displays the XPS survey scan of Ca, Mg, Mn, Cu, P, S and Zn. The binding energies of Ca (FIG. 10B) were discerned to be 347.3 and 350.9 eV (with the splitting of 3.6 eV) which corresponded to the Ca $2p_{3/2}$ and Ca $2p_{1/2}$ states of $Ca^{2+}$. Furthermore, the observed binding energies of the element Mg (88.8 eV), Cu (976.6 eV), P (133.2 eV) and Zn (1022.2 eV) were assigned to the Mg 2s state of $Mg^{2+}$ (FIG. 10C), Cu 2p combined valence state of $Cu^{1+}$ and $Cu^{2+}$ (FIG. 10F), P $2p_{3/2}$ state of $P^{5+}$ (FIG. 10H) and Zn $2p_{312}$ state of $Zn^{2+}$ (FIG. 10E), respectively. See A. A. Aboud, A. Mukherjee, N. Revaprasadu, A. N. Mohamed, The effect of Cu-doping on CdS thin films deposited by the spray pyrolysis technique, J Mater Res Technol 8(2019) 2021-2030, incorporated herein by reference in its entirety. The peaks of S that occurred at 163.2 and 168.4 eV were due to the S $2p_{3/2}$ composed of two oxidation states of $S^{2-}$ and $S^{6+}$ (FIG. 10G). Meanwhile, the peaks appeared at the binding energies of 640.4, 647.5 and 653.7 eV referred to the Mn $2p_{3/2}$ and Mn $2p_{1/2}$ states of $Mn^{3+}$ (FIG. 10D). See E. S. Ilton, J. E. Post, P. J. Heaney, F. T. Ling, S. N. Kerisit, XPS determination of Mn oxidation states in Mn (hydr)oxides, Appl. Surf Sci. 366(2016) 475-485, incorporated herein by reference in its entirety. The XPS data supported the LIBS results, reconfirming the existence of elements Ca, Mg, Mn, Cu, P, S and Zn in the dry MOLs. However, the XPS analyses could not reveal the presence of Na, K and Fe in the dry MOLs which may be due to low detection sensitivity of the XPS instrument for these elements. This disclosure indicated significant advantages of LIBS and ICP-OES measurements to identify and quantify all the elements present in the dry MOLs with the resolution of mg/L/ppb. See T. Trejosa, C. Vander Pyl, K. Menking-Hoggatt, A. L. Alvarado, L. E. Arroyo, Fast identification of inorganic and organic gunshot residues by LIBS and electrochemical methods, Forensic Chem. 8 (2018) 146-156, incorporated herein by reference in its entirety.

Effects of Incident Laser Energy and Time Delay on LIBS Signal Intensity

Figure 3A:
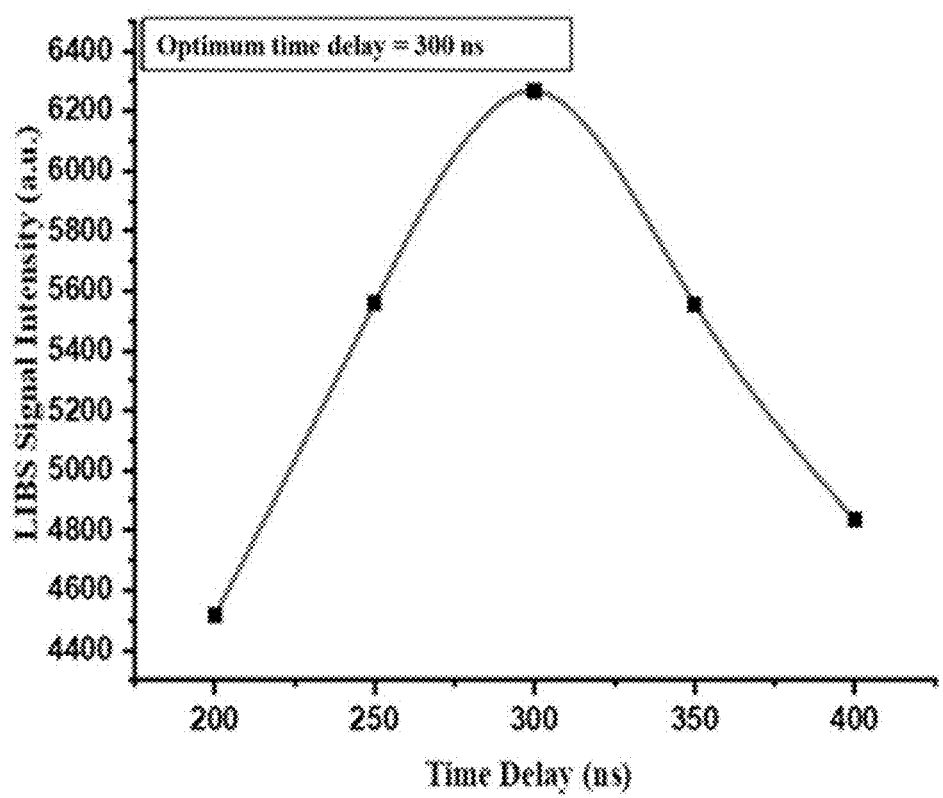
FIG. 3A illustrates the dependence of LIBS signal intensity on the time delay between incident laser pulses (200-400 ns) for the neutral atomic transition line of Ca I monitored at 422.6 nm. A time delay of 300 ns was found to give the highest signal intensity for the MOL samples.
Figure 3B:
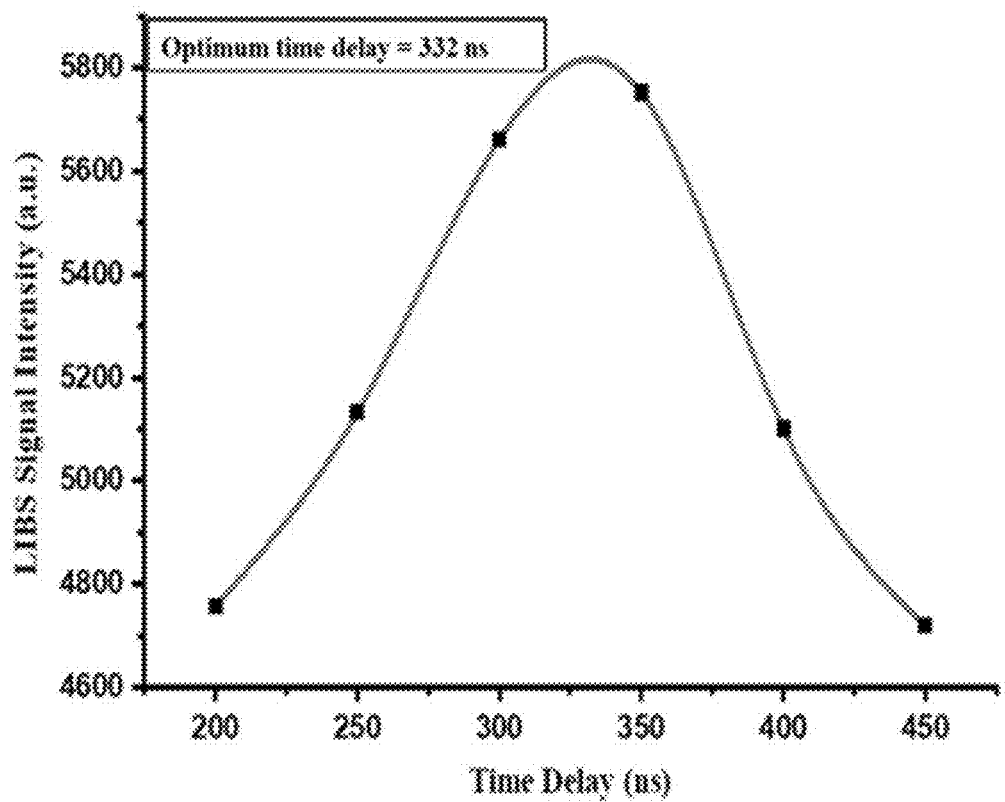
FIG. 3B illustrates the dependence of LIBS signal intensity on the time delay between incident laser pulses (200-400 ns) for the neutral atomic transition line of K I monitored at 769.8 nm. A time delay of 332 ns was found to give the highest signal intensity for the MOL samples.

The optimal time delay of the LIBS measurement was chosen for elements present in the samples of the MOLs. These elements were found to differ in their estimated optimum gated time delay of 300 ns. The dependence of LIBS signal intensity on the time interval between the laser Q-switching and data acquisition via the ICCD camera was examined for the major elements (such as the Ca and K) present in the pellets of the MOLs. The neutral atomic emission spectral line of the CaI and KI were detected at 422.6 nm and 769.8 nm, respectively. The spectra were recorded by accumulating 15 laser pulses each with different gated time delay in the range of 200 to 450 ns. FIGS. 3A and 3B shows the delay time dependent LIBS signal intensity for the CaI and KI transition lines, respectively. The intensity first increased steadily and then reached a maximum at a specific value of the delay time before being decreased. Therefore, the delay time of 300 ns and 332 ns was the optimum value for the detection of the CaI and KI transition lines, respectively.

Different energies of the incident laser pulse were focused on the samples to determine their effects on LIBS signal intensity related to the elements including the neutral Ca and K atoms. The laser excitation energies in the range of 14 to 30 mJ/pulse with an incremental step of 4 mJ were used. The CaI and KI lines were detected at the wavelength of 422.6 nm and 769.8 nm, respectively. The energy of each laser pulse was measured using a digital energy meter (Ophir Model 300). LIBS spectra were recorded by accumulating 15 laser pulses with an excitation-acquisition time delay of 300 ns. The intensity of LIBS signal for both CaI (FIG. 4A) and KI (FIG. 4B) spectral lines was increased linearly with the increase in the excitation energy from 14 to 30 mJ/pulse. The observed linear dependence of LIBS signal intensity on the laser excitation energy was confirmed through the high R-squared fits for the CaI (0.99) and KI (0.99) lines. LIBS signal intensity for both CaI and KI was saturated when the laser energy was over 30 mJ, indicating the attainment of the optimal laser fluence of the recorded transition lines. This observation was attributed to the pulse laser energy mediated increase in the temperature and electron density of the samples. Nonetheless, LIBS signal intensity was saturated when the temperature and electron density became constant, due to the plasma shielding effect. In this process, the radiation of the trailing edge from the incident laser pulse was absorbed via the inverse Bremsstrahlung process and/or reflected by the plasma itself, which in turn prevented the pulse from reaching onto the target surface. See S. S. Harilal, C. V. Bindhu, V. P. N. Nampoori, Temporal and spatial behavior of electron density and temperature in a laser-produced plasma from YBaCuO, Appl. Spectrosc. 52 (1998) 449-455, incorporated herein by reference in its entirety. In addition, the self-absorption by the optically thick plasma contributed to the resultant effect. At a particular wavelength, the emitted radiation from the high-density plasma plume can be regarded as optically thick. The observed resonance lines corresponding to the neutral atomic spectral transitions may have been subjected to the self-absorption process, thereby reducing the peak intensity and broadening the emission lines. See H. Shirvani-Mandavi, S. Z. Shoursheini, H. Gholami, Z. Dini-Torkamani, S. Ghahari-Korani, Calibration-free laser-induced plasma analysis of a metallic alloy with self-absorption correction, Appl. Phys. B 117 (2014) 823-832, incorporated herein by reference in its entirety. To minimize the plasma shielding effect and self-absorption, a chromophore can be added to the MOL sample that will instead absorb the excess energy. Preferable candidates include chromophores which, in the solid state, absorb high energy UV light and have a low quantum yield, thereby reducing the effects the fluorescence signal will have on the overall signal detected for the LIBS measurement. Examples of chromophores include charge transfer compounds and salts thereof such as tetracyanoquinodimethane and tetrathiafulvalene, and fused ring aromatics with inherently low quantum yield (<0.2 D) such as substituted naphthalene, fluorene, and fluorenone derivatives. See J. Oliveira Thermodynamic and optical properties of naphthalene, fluorene and fluorenone derivatives. (2016). Quantum yield is defined as the ratio of the number of photons emitted by the molecule to the number of photons absorbed. Other options include chromophores which absorb light near the excitation wavelength and emit at wavelengths which do not interfere with the signal of the element to be detected. Adding the chromophore to the sample MOL may occur in a multitude of ways. In some embodiments, the chromophore can be mixed into the ground MOL sample before forming the pellet and/or it can be coated onto the front side of the pellet for example, through thermal deposition or spin coating a solution of the chromophore. The front side of the pellet is that on which the laser will be focused during LIBS analysis. The thickness of the chromophore layer on the front side of the pellet should be substantially thin (less than 50 nm) as to still allow the MOL sample to be ablated by the lase pulse.

Validation of Local Thermodynamic Equilibrium and Optical Thinness for Generated Plasma on MOLs Pellets Surface For the reliable analyses of LIBS signal, the laser-induced plasma (LIP) generated on the target (LOMLs pellet) surface must be considered as optically thin and in local thermodynamic equilibrium (LTE). Otherwise, the self-absorption process (re-absorption of the emitted radiation in the plasma itself) becomes dominant and thus distorts the spectral profile (intensity reduction accompanied by the line broadening). This in turn makes quantification of various elements erroneous. See C. Aragon, J. A. Aguilera, Characterization of laser induced plasmas by optical emission spectroscopy: A review of experiments and methods, Spectrochim. Acta. B 63 (2008) 893-916; G. Cristoforetti, A. De Giacomo, M. Dell'Aglio, S. Legnaioli, E. Tognoni, V. Palleschi, N. Omenetto, Local thermodynamic equilibrium in laser-induced breakdown spectroscopy: beyond the McWhirter criterion, Spectrochim. Acta. B 65 (2010) 86-95; H. O. U. Jiajia, L. Zhang, Z. H. A. O. Yang, W. A. A. G. Zhe, Y. Zhang, M. A. Weiguang, J. I. A. Suotang, Mechanisms and efficient elimination approaches of self-absorption in LIBS, Plasma Sources Sci. Technol. 21 (2019)1-15; and R. Yi, L. Guo, C. Li, X. Yang, J. Li, X. Li, X. Zeng, Y. Lu, Investigation of the self-absorption effect using spatially resolved laser-induced breakdown spectroscopy, J. Anal. At. Spectrom. 31 (2016) 961-967, each incorporated herein by reference in their entirety. The LTE condition of the plasma mainly depends on the standard equilibrium population distribution. For example, the relative population of the atomic or ionic excited energy states to the ground energy state can be described by the Boltzmann distribution. The velocities of the free electrons and heavy particles in the plasma follow the Maxwell distribution. The relative population of the two successive ionization stages follows the Saha-Eggert equation. Conversely, the energy distribution of the photons does not follow the Planck's law due to the energy dissipation from the plasma in the form of radiation. To maintain the LTE state of the plasma the collisions among the electrons and ions must be predominating over the radiative processes. Therefore, the plasma must have high electron density to achieve the LTE state. In order to verify the LTE state of the plasma during LIBS measurement, it is important to determine the number density of the electrons ($N_e$) and electron temperature ($T_e$). The threshold (critical or minimum) value of $N_e$ is needed to achieve the LTE state of the plasma which can theoretically be calculated using the McWhirter criterion. See Cristoforetti et al. (2010); G. Cristoforetti, E. Tognoni, L. A. Gizzi, Thermodynamic equilibrium states in laser induced plasmas: From the general case to laser-induced breakdown spectroscopy plasmas, Spectrochim Acta B 90 (2013) 1-22; and S. Zhang, X. Wang, M. He, Y. Jiang, B. Zhang, W. Hang, B. Huang, Laser-induced plasma temperature, Spectrochim Acta B 97 (2014) 13-33, each incorporated herein by reference in their entirety.

The present study applied the Boltzmann plot to evaluate the value of $T_e$ in the LTE state of the optically thin plasma which was generated by the pulse laser ablation of the target (pellets of the MOLs) during LIBS measurement. The Boltzmann plot for the neutral atoms or ions with similar ionization level of a single element having various transition lines can produce a straight line. See Almessiere et al.; Rehana et al.; Aragon et al.; and Zhang et al. This linear plot satisfies the LTE criteria in which the slope ($E_k/K_BT$) provides an estimate of the electron temperature of the plasma. The accurateness of the Boltzmann plot is enhanced when the transition energies of the upper levels occur in a wide range. See Aragón et al.; and Zhang et al. In addition, the precise values of the calculated transition probabilities ($A_{ik}$) and measured emission intensities are the major factors responsible for reducing the errors of the elemental analyses. See A. O. Mehder, M. A. Gondal, M. A. Dastageer, Y. B. Habibullah, M. A. Iqbal, L. E. Oloore, B. Gondal, Direct spectral analysis and determination of high content of carcinogenic bromine in bread using UV pulsed laser induced breakdown spectroscopy, J. Environ. Sci. Health B. 51 (2016) 358-365, incorporated herein by reference in its entirety.

A total of seven well-isolated spectral transition lines corresponding to the neutral CaI was considered to estimate the plasma temperature of the MOLs. FIG. 5 shows the Boltzmann plot of the CaI spectral lines positioned at approximately 428.9, 429.8, 430.7, 442.5, 612.2, 616.2, and 649.3 nm. The observed emission peaks at 428.3, 428.9, 429.8, and 431.8 nm were due to the neutral CaI atom and agreed with other report. See A. R. Striganov, N. S. Sventitskii, Tables of Spectral Lines of Neutral and Ionized Atoms, IFI/Plenum, New York, 1968, incorporated herein by reference in its entirety. Table 1 shows the spectroscopic data of the neutral CaI atomic lines obtained from the NIST database. See NIST Atomic Spectra Database. 2016, http://www.nist.gov/physlab/data/asd. cfm.; and D. R. Lide, CRC Handbook of Chemistry and Physics, Boca Raton, Fla., CRC Press, 2003-2004, each incorporated herein by reference in their entirety. The least square fit to the Boltzmann plot (FIG. 5) produced a high correlation factor of $R^2$=0.98, confirming the LTE state of the plasma. The plasma temperature estimated from the slope of the Boltzmann plot corresponding to the CaI spectral profile was 9767.79±732.3 K. The value of $N_e$ in the plasma corresponding to the CaI transition line (peaked at 442.5 nm) obtained using the McWhirter formula was $0.35 \times 10^{16}$ cm$^{-3}$.

TABLE 1

The basic atomic spectroscopic parameters of the persistent neutral Calcium I (Ca I) lines taken from the NIST database for the estimation of the plasma temperature generated from the laser pulse ablation of the dry MOLs.

| Wavelength (nm) | Element | Signal Intensity | Configurations | Statistical weight $g_i$ | $g_k$ | Transition probability $A_{ik} \times 10^8$ (S$^{-1}$) | Energy of the upper level $E_i$ (eV) | $E_k$ (eV) |
|---|---|---|---|---|---|---|---|---|
| 429.89 | Ca I | 443.2 | $3p^64s4p\ ^3P°_1 \rightarrow 3p^64p^2\ ^3P_1$ | 3 | 3 | 0.466 | 1.885 | 4.769 |
| 430.77 | Ca I | 606.9 | $3p^64s4p\ ^3P°_1 \rightarrow 3p^64p^2\ ^3P_0$ | 3 | 1 | 1.99 | 1.885 | 4.763 |
| 442.54 | Ca I | 556.5 | $3P^64s4p\ ^3P°_0 \rightarrow 3P^64s4d\ ^3D_1$ | 1 | 3 | 0.498 | 1.879 | 4.68 |
| 616.22 | Ca I | 636.1 | $3P^64s4p\ ^3P°_2 \rightarrow 3P^64s5s\ ^3S_1$ | 5 | 3 | 0.345 | 1.899 | 3.91 |
| 649.38 | Ca I | 710.4 | $3P^63d4s\ ^3D_1 \rightarrow 3P^63d4p\ ^3F°_2$ | 3 | 5 | 0.44 | 2.521 | 4.43 |

The Stark broadening mechanism was applied to determine the value of Ne in the studied plasma originated from the pulse laser ablated pellets of the MOLs. The Stark broadening is applicable for plasma with high density (value of $N_e$ at least $\approx 10^{20}$ m$^{-3}$) and low temperature. See J. M. Palomares, S. Hübner, E. A. D. Carbone, N. de Vries, E. M. van Veldhuizen, A. Sola, A. Gamero, J. J. A. M. van der Mullen, $H_\beta$ Stark broadening in cold plasmas with low electron densities calibrated with Thomson scattering, Spectrochim Acta B 73 (2012) 39-47, incorporated herein by reference in its entirety. The electric fields emerged from the oscillating free electrons and ions/atoms during the interactions redistribute the excited energy levels, causing a broadening and shift in the peak position of the spectral line. See Aragon, et al.; and L. J. Radziemski, D. A. Cremers, Handbook of laser induced breakdown spectroscopy, John Wiley & Sons, 2006, each incorporated herein by reference in their entirety. The Stark broadening can be determined from the full width at half maximum (FWHM) of the spectral line via the Lorentzian line shape fitting. The value of Ne of the plasma can be estimated using a previously reported mathematical relation. See Almessiere et al.; Rehana et al.; Harilal et al.; and A. Sarkar, M. Singh, Laser-induced plasma electron number density: Stark broadening method versus the Saha-Boltzmann equation, Plasma Sci. Technol. 19 (2017) 1-9, each incorporated herein by reference in their entirety. This formula connects the value of the FWHM of a Stark broadened spectral line originated from a non-hydrogenic neutral atom or singly charged ion. It considers only the perturbations of the excited energy levels caused by the free electrons rather than those produced by slowly moving singly charged ions. The value of $N_e$ in the plasma was calculated using the CaI spectral line (centered at 442.5 nm with FWHM of 0.038 nm) fitted to the Lorentzian profile (FIG. 6). The values of plasma temperature and electron density was found to be 10000 K and $0.126 \times 10^{17}$ cm$^{-3}$, respectively. See M. S. Dimitrijević, S. Sahal-Bréchot, Stark broadening parameter tables for neutral calcium lines II, Serb. Astron. 161 (2000) 39-88; and M. S. Dimitrijević, S. Sahal-Bréchot, Stark broadening of neutral calcium spectral lines, J. Quant, Spectrosc. Radiat. Transfer 49 (1993) 157-164, each incorporated herein by reference in their entirety. The value of the FWHM was estimated to be 0.063 nm. See Radziemski; and H. R. Griem, Spectral Line Broadening by Plasmas, Academic Press, New York, 1974, each incorporated herein by reference in their entirety. The value of $N_e$ obtained using the experimental value of the FWHM and the Stark width for the CaI line was $\approx 0.31 \times 10^{17}$ cm$^{-3}$.

The threshold value of Ne ($0.35 \times 10^{16}$ cm$^{-3}$) obtained using the McWhirter criterion was compared with the experimentally measured $N_e$ value ($0.31 \times 10^{17}$ cm$^{-3}$). The occurrence of sufficiently large $N_e$ in the plasma enabled more frequent collisions compared to the radiative processes. Therefore, the optical thinness and attainment of the LTE state of the plasma at the MOL pellet surface can be justified if the density criteria are fulfilled during LIBS measurement. Obtaining reproducible and strong LIBS signal from organic compounds is known to be difficult, as signal can vary based on irradiation parameters. Therefore, optimizing these parameters and achieving optical thinness and LTE is crucial for CF-LIBS results. See Moros J, Laserna J. Laser-Induced Breakdown Spectroscopy (LIBS) of Organic Compounds: A Review. Applied Spectroscopy. 2019; 73(9):963-1011, incorporated herein by reference in their entirety.

Qualitative Elemental Analysis of LIBS Spectra Obtained from MOLs

LIBS spectra of the samples recorded in the range of 200 to 800 nm revealed improved signal quality due to reduction of background noise. The detected LIBS spectral peaks corresponding to various elements present in the MOLs were compared with the NIST database. These qualitative elemental analyses of LIBS signal obtained from the dry MOLs clearly demonstrated their remarkable nutritional values beneficial for the human metabolic activities. Table 2 depicts the spectral intensities corresponding to the identified elements present in the dry MOLs.

TABLE 2

The persistent neutral and/or ionic line of the detected elements present in the dry MOLs via the LIBS analyses and the elemental contents using the ICP-OES measurements.

| Elements | Wavelength (nm) | Transition Configuration | LIBS Signal Intensity (a.u.) | ICP-OES concentration (mg L$^{-1}$) |
|---|---|---|---|---|
| Ca | 422.6 | $3p^64s^2\ ^1S_0 \rightarrow 3p^6\ 4s4p\ ^1P^o_1$ | 1389.6 | 21817 |
|  | 445.4 | $3p^6\ 4s4p\ ^3P^o_2 \rightarrow 3p^6\ 4s4d^3D_3$ | 681.6 |  |
|  | 393.3 | $3p^64s\ ^2S_{1/2} \rightarrow 3p^64p\ ^2P^o_{3/2}$ | 1563.9 |  |
|  | 315.8 | $3p^64p\ ^2P^o_{1/2} \rightarrow 3p^6\ 4d\ ^2D_{3/2}$ | 1635.5 |  |
| Cr | — | — | — | Not Detected |
| Cu | 324.7 | $3d^{10}(^1S)\ 4s\ ^2S_{1/2} \rightarrow 3d^{10}\ (^1S)\ 4p\ ^2P^o_{3/2}$ | 150.1 | 12 |
| Fe | 248.3 | $3d^6\ 4s^2\ ^5D_4 \rightarrow 3d^6\ (^5D)4s4p\ (^1P^o)\ ^5F^o_5$ | 435.8 | 696 |
|  | 259.9 | $3d^6\ (^5D)\ 4s\ ^6D_{9/2} \rightarrow 3d^6\ (^5D)\ 4p\ ^6D^o_{9/2}$ | 373.4 |  |
|  | 275.5 | $3d^6\ (^5D)\ 4s\ ^4D_{7/2} \rightarrow 3d^6\ (^5D)\ 4p\ ^4F^o_{9/2}$ | 274.1 |  |
| K | 404.7 | $3p^6\ 4s^2S_{1/2} \rightarrow 3p^6\ 5p\ ^2P^o_{1/2}$ | 756.9 | 14268 |
|  | 766.4 | $3p^6\ 4s\ ^2S_{1/2} \rightarrow 3p^6\ 4p\ ^2P^o_{3/2}$ | 998.6 |  |
|  | 769.8 | $3p^6\ 4s\ ^2S_{1/2} \rightarrow 3p^6\ 4p\ ^2P^o_{1/2}$ | 961.8 |  |
| Mg | 279.5 | $3p^6\ 3s\ ^2S_{1/2} \rightarrow 3p^6\ 3p\ ^2P^o_{3/2}$ | 623.4 | 4440 |
|  | 280.2 | $3p^6\ 3s\ ^2S_{1/2} \rightarrow 3p^6\ 3p\ ^2P^o_{1/2}$ | 475.4 |  |
|  | 285.2 | $2p^6\ 3s^2\ ^1S_0 \rightarrow 3s3p\ ^1p\ ^1P^o_1$ | 571.8 |  |
| Mn | 403.0 | $3d^54s^2\ ^6S_{5/2} \rightarrow 3d^5(^6S)\ 4s4p\ (^3P^o)\ ^6P^o_{7/2}$ | 208.1 | 81 |
|  | 257.6 | $3d^5\ (^6S)4s\ ^7S_3 \rightarrow 3d^5\ (^6S)\ 4p\ ^7P^o_4$ | 251.5 |  |
|  | 259.3 | $3d^5\ (^6S)4s\ ^7S_3 \rightarrow 3d^5\ (^6S)\ 4p\ ^7P^o_3$ | 166.8 |  |
| Na | 328.5 | $2s^2\ 2p^5\ 3s\ ^1P^o_1 \rightarrow 2s^2\ 2p^5\ 3p\ ^1D_2$ | 428.6 | 1072 |
|  | 588.9 | $2p^6\ 3s\ ^2S_{1/2} \rightarrow 2p^6\ 3p\ ^2P^o_{3/2}$ | 464.8 |  |
|  | 589.5 | $2p^6\ 3s\ ^2S_{1/2} \rightarrow 2p^6\ 3p\ ^2P^o_{1/2}$ | 369.8 |  |
| P | 253.5 | $3s^2\ 3p^3\ ^2P^o_{3/2} \rightarrow 3s^2\ 3p^2(^3P)\ 4s\ ^2P_{3/2}$ | 276.5 | 2800 |
|  | 255.3 | $3s^2\ 3p^3\ ^2P^o_{1/2} \rightarrow 3s^2\ 3p^2(^3P)\ 4s\ ^2P_{1/2}$ | 226.0 |  |
| S | 543.2 | $3s^2\ 3p^2(^3P)\ 4s\ ^4P_{3/2} \rightarrow 3s^2\ 3p^2\ (^3P)\ 4p\ ^4D^o_{5/2}$ | 448.9 | 8336 |
|  | 545.3 | $3s^2\ 3p^2(^3P)\ 4s\ ^4P_{5/2} \rightarrow 3s^2\ 3p^2\ (^3P)\ 4p\ ^4D^o_{7/2}$ | 552.1 |  |
| Se | — | — | — | Not Detected |
| Zn | 250.1 | $3d^{10}\ 4p\ ^2P^o_{1/2} \rightarrow 3d^{10}\ 5s\ ^2S_{1/2}$ | 89.4 | 29 |
|  | 255.7 | $3d^{10}\ 4p\ ^2P^o_{3/2} \rightarrow 3d^{10}\ 5s\ ^2S_{1/2}$ | 146.9 |  |
|  | 334.5 | $3d^{10}\ 4s4p\ ^3P^o_2 \rightarrow 3d^{10}\ 4s4d^3\ ^3D_3$ | 144.9 |  |

FIGS. 7, 8 and 9 show LIBS spectra of the dry MOLs in the range of 200-350 nm, 380-450 nm, and 500-800 nm, respectively. The spectra revealed several atomic and ionic spectral lines with different intensities, confirming the existence of major nutritional elements (Ca, Na, K, Fe, Mg, Mn, Cu, P, S and Zn) in the dry MOLs. In addition, the amount of Ca, K, Mg, P, and S present in the MOLs were higher than the other elements. Most of the identified elements in the dry MOLs showed multiple characteristic atomic peaks including the Ca (centered at 422.6, 445.4, 393.3 and 315.8 nm), Na (centered at 328.5, 588.9 and 589.5 nm), Mg (centered at 279.5, 280.2 and 285.2 nm), K (centered at 404.7, 766.4, and 769.8 nm), Fe (centered at 248.3, 259.9 and 275.5 nm), Mn (centered at 403.0, 257.6 and 259.3 nm), Cu (centered at 324.7 nm), P (centered at 253.5 and 255.3 nm), S (centered at 543.2 and 545.3 nm) and Zn (centered at 250.1, 255.7 and 334.5 nm). It is worth mentioning that the elements Ca, Mn, Cu and P are essential for the generation and reinforcement of human bones and teeth. Meanwhile, the element K is required for maintaining the right blood pressure, cleanliness of the skin and induction of the kidneys to get rid of deleterious wastes. In addition, potassium together with P and Ca enable the human brain to acquire oxygen for modulating neuromuscular activities. The element Mg is indispensable in the human body for protein production, cellular reproduction, and proper functioning of the thyroid gland. On top, the element Mg plus Ca are vital for controlling the contraction and relaxation of muscles. Likewise, the elements Fe and Cu are responsible for carrying the oxygen in hemoglobin, myoglobin and red blood cells of the human. Generally, the element Zn contributes to growth of the human body. Conversely, the element S participates in the synthesis of certain key proteins that act as the effective antioxidants and protect human cells from damage. See Alresawum et al.; Anwar et al.; and B. Omolaso, O. A. Adegbite, S. A. Seriki, I. I. Ndukwe, Effects of *Moringa oleifera* on Blood Pressure and Blood Glucose Level in Healthy Humans, Br J. Med Health Res. 3 (2016) 22-34, each incorporated herein by reference in their entirety.

Calibration-Free LIBS (CF-LIBS)

The CF-LIBS technique was used for quantitative elemental analysis of the samples. This measurement did not require any calibration curve and avoided problems related to matrix compositions because the produced plasma was known to be in LTE state and optically thin. The LIBS system was optimized with respect to the electron temperature, electron density, incident laser energy and time delay to confirm the optical thinness and LTE state of the plasma generated by the laser pulse ablation of the MOLs pellet. The contents of various elements in the dry MOLs were determined as a function of the plasma temperature and electron density of the neutral and singly ionic species obtained by analyzing the measured plasma emission spectral line intensities. The integrated intensity of the measured spectral line is written as:

$$I_\lambda^{ki} = FC_s A_{ki} \frac{g_k}{U_s(T)} \exp\left(\frac{-E_k}{K_B T}\right) \quad (1)$$

where k and i are the indices of the upper and lower transition energy levels, is the transition wavelength between the upper ($E_k$) and lower ($E_i$) energy level, F is an experimental parameter that considers the optical efficiency of the collection system and total plasma density, $C_s$ is the concentration of the emitting species s, $A_{ki}$ is the transition probability for the spontaneous emission from the state k to i, $g_k$ is the degeneracy of the k level, $K_B$ is the Boltzmann constant, T is the plasma temperature, and U(T) is the partition function of the emitting species s at the plasma temperature T. See H. R. Griem, Principles of Plasma Spectroscopy, Cambridge University Press, 1997, incorporated herein by reference in its entirety. The value of U(T) can be calculated using the expression:

$$U(T) = \Sigma g_k \exp\left(\frac{-E_k}{K_B T}\right) \quad (2)$$

The spectral parameters used in the CF-LIBS analyses were obtained from the NIST database [1]. Table 1 and 2 enlists the values of F, Cs, and T. The factor F can be evaluated in terms of $$q_s = \ln\left(\frac{C_s F}{U(T)}\right)$$

using the normalization condition given by:

$$\sum_s C_s = \frac{1}{F} U_s(T) \exp(q_s) = 1 \quad (3)$$

The concentration of the species s in the sample can be calculated via:

$$C_s = \frac{1}{F} U_s(T) \exp(q_s) \quad (4)$$

The estimated content of various elements present in the dry MOLs was found to be Ca=21849 mg L$^{-1}$, Cu=9 mg L$^{-1}$, Fe=663 mg L$^{-1}$, K=14301 mg L$^{-1}$, Mg=4500 mg L$^{-1}$, Mn=77 mg L$^{-1}$, Na=1113 mg L$^{-1}$, P=2661 mg L$^{-1}$, Zn=19 mg L$^{-1}$, and S=7929 mg L$^{-1}$ (Table 3). A comparison between the results obtained from the CF-LIBS and ICP-OES analysis (Table 3) for the elemental contents present in the dry MOLs revealed an excellent agreement.

TABLE 3

Comparison between the CF-LIBS and standard ICP-OES results for the detected elements in the dry MOLs
Comparison of LIBS and ICP, and RA

| Elements detected in MOLs | CF-LIBS (mg L$^{-1}$) | ICP-OES (mg L$^{-1}$) | RA | Standard deviation CF-LIBS |
|---|---|---|---|---|
| Ca | 21849 | 21817 | 0.02 | 0.07 |
| Na | 1113 | 1072 | 0.38 | 0.11 |
| K | 14301 | 14268 | 0.03 | 0.07 |
| Mg | 4500 | 4440 | 0.14 | 0.09 |
| Fe | 663 | 696 | 0.47 | 0.12 |
| Mn | 77.6 | 81 | 0.42 | 0.12 |
| Zn | 19.14 | 29 | 0.34 | 0.11 |
| P | 2661 | 2800 | 0.49 | 0.13 |
| S | 7929 | 8336 | 0.49 | 0 13 |
| Cu | 9.1 | 12 | 0.24 | 0.10 |

Comparison of Data from Two Detection Techniques and LIBS Accuracy

To reaffirm the reliability of the CF-LIBS outcome for the quantified elements present in the MOLs samples, the results were compared to that of ICP-OES analyses. Fifteen laser pulses were accumulated to get the average CF-LIBS spectra, which reduced the standard deviation (SD) when the number of the laser shots was increased. The relative accuracy (RA) was calculated using the expression [5]:

$$RA = \frac{|d| + SD \times \frac{t_{0.975}}{\sqrt{n}}}{M} \quad (5)$$

where d is the difference between CF-LIBS and ICP-OES data (standard method), M is the measurement using the ICP-OES technique, n is the number of measurements, and to 975 is the t-value at a 2.5% error of confidence. The relative accuracy of the developed CF-LIBS system was within the range of 0.02 to 0.49 (Table 3), indicating the excellent acceptability of the state-of-the-art technique for accurate quantification of the elemental compositions in the dry MOLs.

The invention claimed is:

1. A method of determining the micronutrient profile of a *Moringa oleifera* leaf comprising:
   drying the *Moringa oleifera* leaf at a temperature less than 100° C. to form a dried leaf;
   grinding the dried leaf to form a homogeneous mixture;
   compressing the homogeneous mixture into a pellet comprising a chromophore;
   analyzing the elemental composition of said pellets with calibration free laser-induced breakdown spectroscopy (CF-LIBS); and
   wherein the analyzing is carried out with a CF-LIBS algorithm configured to calculate the quantity of a plurality of elements selected from the group Ca, Cu, Fe, K, Mg, Mn, Na, P, S, and Zn present in the pellets; and
   wherein the CF-LIBS is performed using a pulsed laser having a pulse width of 5 to 10 ns, a repetition rate of 15 to 25 Hz, a time delay of 290 to 350 ns, and a laser energy of 10 to 30 mJ.

2. The method of claim 1, further comprising:
   determining the concentration of a set of elements in an Nth sample of *Moringa oleifera* leaves using laser-induced breakdown spectroscopy to produce an Nth sample element profile, wherein the calculating comprises mixing variable amounts of the first through Nth samples to produce a composite dose comprising at least two of the first through Nth samples.

3. The method of claim 1, wherein the spectra of at least 2 laser pulses are accumulated to get the average CF-LIBS spectrum.

4. The method of claim 1, wherein the pellets are mounted on the top of a two-dimensional motorized translational stage during CF-LIBS analysis.

5. The method of claim 1, wherein the detected element during CF-LIBS analysis is Ca and at least one atomic line at 422.6, 445.4, 393.3 and 315.8 nm is monitored; and the optimum gated time delay of the pulsed laser is 300 ns.

6. The method of claim 1, wherein the detected element during CF-LIBS analysis is K and at least one atomic line at 404.7, 766.4, and 769.8 nm is monitored; and the optimum gated time delay of the pulsed laser is 332 ns.

7. The method of claim 1, wherein the detected element during CF-LIBS analysis is Cu and the atomic line at 324.7 nm is monitored.

8. The method of claim 1, wherein the detected element during CF-LIBS analysis is Fe and at least one atomic line at 248.3, 259.9, and 275.5 nm is monitored.

9. The method of claim 1, wherein the detected element during CF-LIBS analysis is Mg and at least one atomic line at 279.5, 280.2, and 285.2 nm is monitored.

10. The method of claim 1, wherein the detected element during CF-LIBS analysis is Mn and at least one atomic line at 403.0, 259.3, and 257.6 nm is monitored.

11. The method of claim 1, wherein the detected element during CF-LIBS analysis is Na and at least one atomic line at 328.5, 588.9, and 589.5 nm is monitored.

12. The method of claim 1, wherein the detected element during CF-LIBS analysis is P and at least one atomic line at 253.5 and 255.3 nm is monitored.

13. The method of claim 1, wherein the detected element during CF-LIBS analysis is S and at least one atomic line at 543.2 and 545.3 nm is monitored.

14. The method of claim 1, wherein the detected element during CF-LIBS analysis is Zn and at least one atomic line at 250.1, 255.7, and 334.5 nm is monitored.

15. The method of claim 1, wherein the sensitivity is sufficient to detect 1 mg/L of at least one of Ca, Cu, Fe, K, Mg, Mn, Na, P, S, and Zn in the *Moringa oleifera* leaves.

16. The method of claim 1, wherein the CF-LIBS algorithm assumes the sample is in local thermodynamic equilibrium (LTE); and LTE is determined by the number density of electrons and electron temperature in the plasma during the CF-LIBS measurements; and the electron temperature is between 9,000 to 10,000 K; and the number density of electrons is $0.10 \times 10^{16}$ to $0.50 \times 10^{17}$ cm$^{-3}$.

17. The method of claim 1 further comprising:

validating the micronutrient profile results of CF-LIBS by comparing to the standard method of elemental detection using ICP-OES wherein the relative accuracy is in the range of 0.01 to 0.50.

18. The method of claim 1, wherein the chromophore is a fused ring aromatic compound.

19. The method of claim 18, wherein the fused ring aromatic compound is selected from the group comprising substituted naphthalene, fluorene, and fluorenone derivatives.

20. The method of claim 1, wherein the chromophore is mixed into the homogeneous mixture before being compressed into a pellet and/or the chromophore is coated onto the side of the pellet onto which the laser will be focused.

* * * * *